US012751801B2

(12) United States Patent
Gandrud et al.

(10) Patent No.: US 12,751,801 B2
(45) Date of Patent: Oct. 6, 2026

(54) VALIDATION FOR THE PLACEMENT AND GENERATION OF COMPONENTS FOR DENTAL RESTORATION APPLIANCES

(71) Applicant: Solventum Intellectual Properties Company, Maplewood, MN (US)

(72) Inventors: Jonathan D. Gandrud, Woodbury, MN (US); Marie D. Manner, St. Paul, MN (US); Joseph C. Dingeldein, Hudson, WI (US); James D. Hansen, White Bear Lake, MN (US); John A. Norris, Woodbury, MN (US); Jianbing Huang, Shoreview, MN (US); Seyed Amir Hossein Hosseini, St. Paul, MN (US); Wenbo Dong, Lakeville, MN (US)

(73) Assignee: Solventum Intellectual Properties Company, Eagan, MN (US)

( * ) Notice: Subject to any disclaimer, the term of this patent is extended or adjusted under 35 U.S.C. 154(b) by 0 days.

(21) Appl. No.: 18/874,711

(22) PCT Filed: Jun. 14, 2023

(86) PCT No.: PCT/IB2023/056142
§ 371 (c)(1),
(2) Date: Dec. 13, 2024

(87) PCT Pub. No.: WO2023/242761
PCT Pub. Date: Dec. 21, 2023

(65) Prior Publication Data

US 2025/0375272 A1 Dec. 11, 2025

Related U.S. Application Data

(60) Provisional application No. 63/366,507, filed on Jun. 16, 2022.

(51) Int. Cl.
*A61C 13/00* (2006.01)
*G16H 20/40* (2018.01)
(Continued)

(52) U.S. Cl.
CPC ......... *A61C 13/0004* (2013.01); *G16H 20/40* (2018.01); *G16H 30/40* (2018.01); *G16H 50/50* (2018.01)

(58) Field of Classification Search
CPC .... A61C 13/0004; G16H 20/40; G16H 30/40; G16H 50/50; G16H 30/20
See application file for complete search history.

(56) References Cited

U.S. PATENT DOCUMENTS

2007/0238065 A1 10/2007 Sherwood et al.
2020/0085546 A1 3/2020 Li et al.
(Continued)

FOREIGN PATENT DOCUMENTS

EP 3462373 A1 * 4/2019 ........... G06V 20/653
EP 3591616 A1 1/2020
(Continued)

OTHER PUBLICATIONS

Xu X, Liu C, Zheng Y. 3D Tooth Segmentation and Labeling Using Deep Convolutional Neural Networks. IEEE Trans Vis Comput Graph. Jul. 2019;25(7):2336-2348. doi: 10.1109/TVCG.2018.2839685. Epub May 22, 2018. PMID: 29994311 (Year: 2019).*
(Continued)

*Primary Examiner* — Linh Giang Le

(57) ABSTRACT

Systems and techniques for training one or more neural networks to automatically validate geometrical characteristics of a digital representation of a dental restoration appliance component are disclosed including analyzing one or more assigned labels, automatically generating output that specifies whether the dental restoration appliance is incor-
(Continued)

rect, automatically training the neural network based on the one or more result labels assigned by the neural network.

20 Claims, 13 Drawing Sheets

(51) Int. Cl.
*G16H 30/40* (2018.01)
*G16H 50/50* (2018.01)

(56) References Cited

U.S. PATENT DOCUMENTS

| | | | | |
|---|---|---|---|---|
| 2021/0082184 | A1* | 3/2021 | Claessen | G06N 3/08 |
| 2022/0218449 | A1* | 7/2022 | Azernikov | A61C 13/0004 |
| 2022/0262007 | A1 | 8/2022 | Cramer et al. | |

FOREIGN PATENT DOCUMENTS

| | | | |
|---|---|---|---|
| WO | 2019058243 | A1 | 3/2019 |
| WO | 2019069191 | A2 | 4/2019 |
| WO | 2020026117 | A1 | 2/2020 |
| WO | 2020136587 | W | 7/2020 |
| WO | 2020240351 | A1 | 12/2020 |
| WO | 2021240290 | A1 | 12/2021 |
| WO | 2022123402 | A1 | 6/2022 |

OTHER PUBLICATIONS

International Search Report for PCT International Application No. PCT/IB2023/056142, mailed on Sep. 14, 2023, 4 pages.

MeshCNN: A Network with an Edge, ACM Transactions on Graphics, vol. 1, No. 1, Feb. 2019, [retrieved from the internet on Jan. 18, 2023], URL <https://arxiv.org/abs/1809.05910>, 12 pages.

* cited by examiner

VALIDATION FOR THE PLACEMENT AND GENERATION OF COMPONENTS FOR DENTAL RESTORATION APPLIANCES

CROSS REFERENCE TO RELATED APPLICATIONS

This application is a national stage filing under 35 U.S.C. 371 of PCT/IB2023/056142, filed Jun. 14, 2023, which claims the benefit of U.S. Provisional Application No. 63/366,507, filed Jun. 16, 2022, the disclosure of which is incorporated by reference in its/their entirety herein.

TECHNICAL FIELD

The present disclosure relates to various improved machine learning techniques used in digital oral care which includes the disciplines of digital dentistry and digital orthodontics.

BACKGROUND

Dental practitioners often utilize dental appliances to re-shape or restore a patient's dental anatomy or utilize orthodontic appliances to move the teeth. These appliances are typically constructed from a model of the patient's dental anatomy, which are modified to a desired final state. The model may be a physical model or a digital model. Historically, systems performed operations on 2D images of dental tissue (or dental or orthodontic appliances) and then projected the resulting data from those 2D images back onto the corresponding 3D mesh geometry (e.g., to label portions of the mesh). Some of those systems were configured to operate on photographs while others were configured to operate on height maps. Problems with past approaches included loss of accuracy in the mapping, and the inefficient processing of the data to generate a 2D to 3D conversion.

For instance, according to existing embodiments, projection operations performed by existing systems may cause a 3D mesh element to receive conflicting labels as the result of two or more projection operations. This can result in the need to perform additional machine learning models to disambiguate those conflicting labels, which adds to the complexity and error of the overall system.

DETAILED DESCRIPTION

Figure 1:
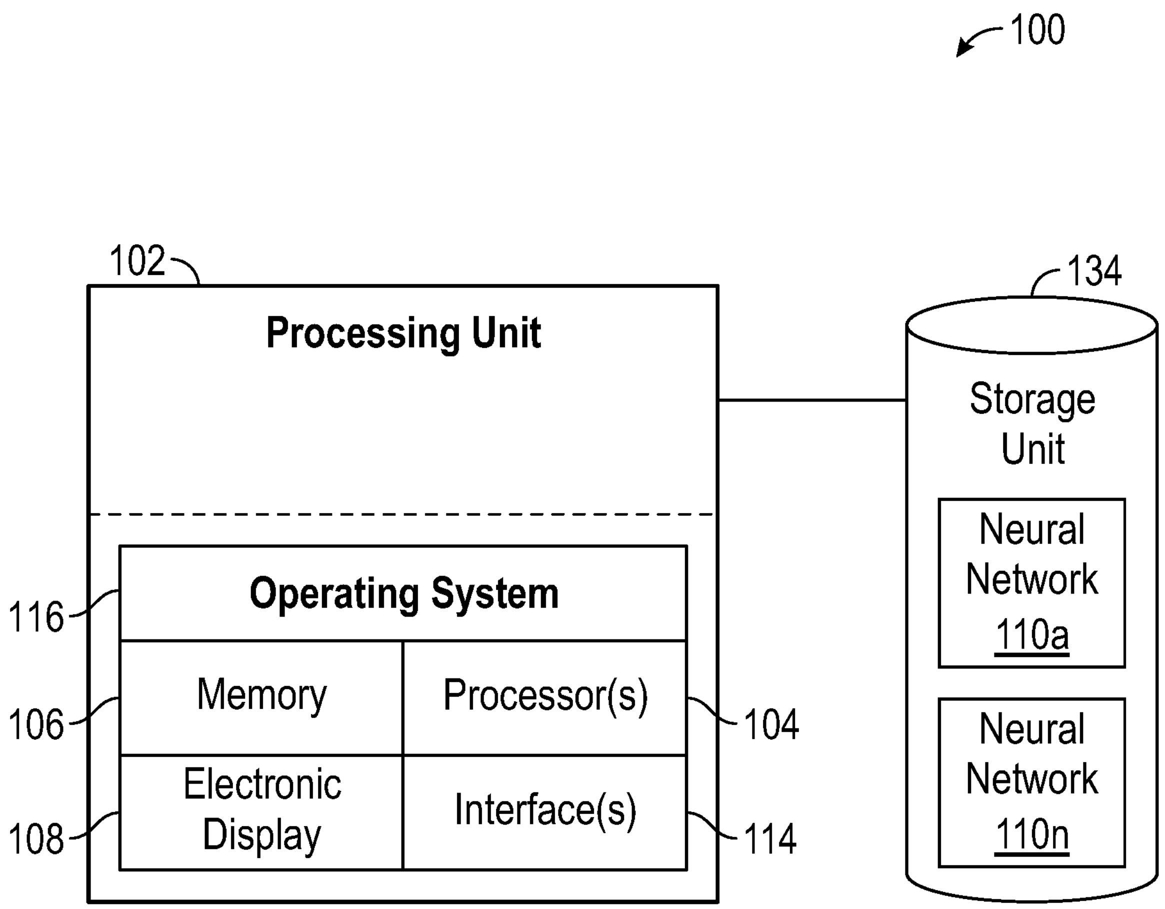
FIG. 1 shows an example processing unit that operates in accordance with the techniques of the disclosure.

This disclosure describes various automation techniques that can be implemented throughout the process of fabricating dental and orthodontic appliances. As a result, the present disclosure contemplates improvements to areas of digital oral care which includes the disciplines of digital dentistry and digital orthodontics. The automated geometry generation techniques of this disclosure are intended to streamline fabrication processes which would otherwise be extremely time consuming. A further advantage of these automated geometry generation techniques is to improve the accuracy of the dental appliance. An algorithm may in some instances produce geometry which is of higher quality and accuracy than the geometry produced by the human technician. Whereas in some instances, a human technician may make modifications or "tweaks" to a design that is output from the automation tools, the automation tools improve the quality of the resulting appliance by providing multiple technicians with a common baseline upon which to build. Furthermore, an untrained or new human technician can learn about the proper techniques for creating dental and orthodontic appliances (used generically herein as an oral care appliance) by studying the outputs of the automation tools in this disclosure (e.g., both the tools for geometry generation and the tools for geometry validation). Knowledge transfer to other technicians and the standardization of technique are important benefits of the techniques of this disclosure. For all the above reasons, another advantage is that more accurate geometries and knowledge transfer can improve restorative outcomes related to the use of the fabricated dental or orthodontic appliance.

Historically, systems performed operations on 2D images of dental tissue (or dental or orthodontic appliances) and then projected the resulting data from those 2D images back onto the corresponding 3D mesh geometry (e.g., to label portions of the mesh). Some of those systems were configured to operate on photographs while others were configured to operate on height maps. The techniques disclosed herein take a more direct approach in that mesh elements are directly labeled, without the need for intermediate 2D images and the projection of information from those 2D images onto 3D meshes. As a result, for example, direct labeling of 3D mesh elements for the segmentation and mesh cleanup can be performed, which is not possible using existing systems that rely on 2D mapping techniques. This approach of direct element labeling leads to greater accuracy of the underlying machine learning (ML) model and provides for greater efficiency regarding the use of computational resources because the computational overhead of generating images as well as mapping images back onto 3D geometry can be avoided.

As is used herein, a 3-dimensional ("3D") mesh (or 3D geometry) includes data corresponding to edges, vertices, and faces of the 3D mesh. These edges, vertices, and faces are also referred to as one or more aspects of a digital representation, such as a 3D mesh. In some examples, an aspect of a 3D mesh may refer to the shape or geometrical characteristics of that mesh. The aspects of one mesh may, in some instances, be compared to the aspects of another mesh, for example in the course of a validation operation. Though interrelated, these three types of data are distinct. The vertices are the points in 3D space that define the boundaries of the mesh. Accordingly, without the additional information of how the points are connected to each other, these points can be thought of as a point cloud. In the context of a 3D mesh, however, the edges provide structure to the point cloud. An edge includes two points and can also be referred to as a line segment. A face includes both the edges and the vertices. For instance, in the case of a triangle mesh, a face includes three vertices, where the vertices are interconnected to form three contiguous edges. While 3D meshes are commonly formed using triangles, other implementations may define 3D meshes using quadrilaterals, pentagons, or some other n-sided polygon. Some meshes may contain degenerate elements, such as non-manifold geometry. Non-manifold geometry is digital geometry that cannot exist in the real world. For instance, one definition of non-manifold is a 3D shape that cannot be unfolded into a 2D surface so that the unfolded shape has all its surface normal vectors pointing in the same direction. One example of when non-manifold geometry can occur is where a face or edge is extruded but not moved, which results in two identical edges being formed on top of each other. Typically, this non-manifold geometry is removed before processing can proceed. Other mesh pre-processing operations are also possible. The 3D data for each of the examples in this disclosure may be presented to an ML model as a 3D mesh and/or output from the ML model as a 3D mesh. Other 3D data representations include voxels, finite elements, finite differences, discrete elements and other 3D geometric representations of dental data and/or appliances. Other implementations may describe 3D geometry using non-discrete methods, whereby the geometry is regenerated at the time of processing using mathematical formulas. Such formulas may contain expressions including polynomials, cosines and/or other trigonometry or algebraic terms. One advantage of non-discrete formats may be to compress data and save storage space. Digital 3D data may entail different coordinate systems, such as XYZ (Euclidean), cylindrical, radial, and custom coordinate systems.

That is, a 3D mesh is a data structure which may describe the structure, geometry and/or shape of an object related to oral care, including but not limited to a tooth, a hardware element, or a patient's gum tissue. The geometry of a 3D mesh may define aspects of the physical dimensions, proportions and/or symmetry of the mesh. The structure of the 3D mesh may define the count, distribution and/or connectivity of mesh elements. A 3D mesh may include one or more mesh elements such as one or more vertices, edges, faces, and combinations thereof. In some implementations, mesh elements may include voxels, such as in the context of sparse mesh processing operations. Various spatial and structural features may be computed for these mesh elements and be provided to the predictive models of this disclosure with the advantage of improving the accuracy of those predictive models. For instance, a mesh element feature may, in some implementations, quantify some aspect of a 3D mesh in proximity to or in relation with one or more mesh elements, as described elsewhere in this disclosure.

According to particular implementations, it may be beneficial to pre-process information to generate one or more mesh feature elements. That is, each 3D mesh may undergo pre-processing before being input to the predictive architecture (e.g., including at least one of an encoder, decoder, autoencoder, multilayer perceptron (MLP), transformer, pyramid encoder-decoder, U-Net or a graph CNN). This pre-processing may include the conversion of the mesh into lists of mesh elements, such as vertices, edges, faces or in the case of sparse processing—voxels. For the chosen mesh element type or types, (e.g., vertices), feature vectors may be generated. In some examples, one feature vector is generated per vertex of the mesh. Each feature vector may contain a combination of spatial and/or structural features, as specified by the following table:

TABLE 1

| Element | Spatial Features | Structural Features |
|---|---|---|
| Edges | XYZ position of an edge midpoint, XYZ positions of the edge vertices, and the normal vector at an edge midpoint (average of the normal vectors of two vertices). | Edge curvature (depends on a connectivity neighborhood, average curvature of two vertices), dihedral angles, edge length, density measure such as a count of incident edges (i.e., a count of the other neighboring edges which share the vertices of that edge). |
| Faces | XYZ position of a face centroid, surface normal vector. | Face curvature (average curvature of the vertices of the face), face area, density measure such as count of adjacent faces (i.e., which share at least one edge with the face). |
| Vertices | XYZ position, normal vector (weighted average of normal vectors of the connecting faces for the vertex). | Vertex curvature, density measure such as the count of vertices within a radius of the vertex, density measure such as the count of incident edges. |
| Voxels | XYZ centroid. | Volume, [height × depth × width] dimensions, density measure such as a count of contained vertices, density measure such as count of intersected faces, density measure such as count of intersected edges. |

Consistent with Table 1, a voxel may also have features which are computed as the aggregates of the other mesh elements (e.g., vertices, edges and faces) which either intersect the voxel or, in some implementations, are predominantly or fully contained within the voxel. Rotating the mesh may not change structural features but may change spatial features. And, as described elsewhere, the term "mesh" should be considered in a non-limiting sense to be inclusive of 3D mesh, 3D point cloud and 3D voxelized representation. In some instances, a 3D point cloud may be derived from the vertices of a 3D triangle mesh.

Techniques which may operate on feature vectors of the aforementioned features include but are not limited to: mesh reconstruction autoencoder, mesh segmentation, mesh segmentation validation, coordinate system prediction, coordinate system validation, mesh cleanup, mesh cleanup validation, chairside intraoral dental scan validation, clear tray aligners (CTA) setups validation, bracket/attachment/hardware placement validation, generating a custom oral care appliance component, placing a custom oral care appliance component, the validation of custom oral care appliances (e.g., such as validating the shape or placement of a dental restoration appliance component), restoration design generation, restoration design generation validation, fixture model validation and CTA trimline validation. Such feature vectors may be presented to the input of a predictive model. In some implementations, such feature vectors may be presented to one or more internal layers of a neural network which is part of one or more of those predictive models.

But 3D meshes are only one type of 3D representation that can be used. Thus, it should be understood, without loss of generality, that there are various types of 3D representations contemplated herein. For instance, a 3D representation may include, be, or be part of one or more of a 3D polygon mesh, a 3D point cloud, a 3D voxelized representation (e.g., a collection of voxels), or 3D representations which are described by mathematical equations. Although the term "mesh" is used frequently throughout this disclosure, the term should be understood, in some implementations, to be interchangeable with other types of 3D representations. A 3D representation may describe elements of the 3D geometry and/or 3D structure of an object. And a patient's dentition may include one or more 3D representations of the patient's teeth, gums and/or other oral anatomy. According to particular implementations, an initial 3D representation may be produced using a 3D scanner, such as an intraoral scanner, a computerized tomography (CT) scanner, ultrasound scanner, a magnetic resonance imaging (MRI) machine or a mobile device which is enabled to perform stereophotogrammetry.

In accordance with the above, the techniques described herein relate to operations that are performed on 3D representations to perform tasks related to geometry generation and/or validation. For instance, the present disclosure relates to improved automated techniques for segmentation generation and validation, coordinate system prediction and validation, clear tray aligner setups validation, dental restoration appliances validation, bracket and attachment (or other hardware) placement and validation, 3D printed parts validation, restoration design generation and validation, and fixture models validation, and clear tray aligner trimline validation, to name a few examples. The present disclosure also relates to improved automated techniques for the validation of many of those examples.

In general, the use of edge information ensures that the ML model is not sensitive to different input orders of 3D elements. One notable exception is the implementation for coordinate system prediction, which operates on 3D point clouds, rather than 3D meshes. These and other distinctions will be described in more detail below.

Certain examples in this disclosure mention the use of either a MeshCNN or an Encoder for the processing of 3D mesh geometries (e.g., an encoder structure for 3D validation and bracket/attachment placement, and a MeshCNN for labeling mesh elements in segmentation and mesh cleanup). Without limitation, each of these examples may also employ other kinds of neural networks for the handling of 3D mesh geometry, either in addition to the specified neural network or in place of the specified neural network. The following neural networks may be interchanged in various implementations of the 3D mesh geometry examples of this disclosure: ResNet, U-Net, DenseNet, MeshCNN, Graph-CNN, PointNet, multilayer perceptron (MLP), PointNet++, PointCNN, and PointGCN. In other instances, an encoder structure may be used.

Systems of this disclosure may, in some instances, be deployed in a clinical setting (such as a dental or orthodontic office) for use by clinicians (e.g., doctors, dentists, orthodontists, nurses, hygienists, oral care technicians). Such systems which are deployed in a clinical setting may enable clinicians to process oral care data (such as dental scans) in the clinic environment, or in some instances, in a "chairside" context (e.g., in near "real-time" where the patient is present in the clinical environment). A non-limiting list of examples of techniques may include: segmentation, mesh cleanup, coordinate system prediction, CTA trimline generation, restoration design generation, appliance component generation or placement or assembly, generation of other oral care meshes, the validation of oral care meshes, setups prediction, removal of hardware from tooth meshes, hardware placement on teeth, imputation of missing values, clustering on oral care data, oral care mesh classification, setups comparison, metrics calculation, or metrics visualization. The execution of these techniques may, in some instances, enable patient data to be processed, analyzed and used in appliance creation by the clinician before the patient leaves the clinical environment (which may facilitate treatment planning because feedback may be received from the patient during the treatment planning process).

Systems of this disclosure may train ML models with representation learning. The advantages of representation learning include the fact that the generative network (e.g., neural network that predicts the transform) is guaranteed to receive input with a known size and/or standard format, as opposed to receiving input with a variable size or structure. Representation learning may produce improved performance over other methods, since noise in the input data may be reduced (e.g., since the representation generation model extracts the important aspects of a inputted mesh or point cloud through loss calculations or network architectures chosen for that purpose). Such loss calculation methods include KL-divergence loss, reconstruction loss or other losses disclosed herein. Representation learning may reduce the size of dataset required for training the model, since the representation model learns the representation, the generative network may focus on learning the generative task. The result may be improved model generalization because meaningful features are made available to the generative network. In some instances, transfer learning may first train a representation generation model. That representation generation model (in whole or in part) may then be used to pre-train a subsequent model, such as a generative model (e.g., that generates transform predictions).

A dental restoration appliance may be designed in digital form through automated mesh processing or machine learning operations (or both) to place appliance components relative to representations of the patient's dentition and/or generate appliance components which are tailored to the contours, landmarks or other aspects of the patient's dentition. PCT Patent Application WO2020240351A1 (the entirety of which is incorporated herein by reference) describes techniques to place appliance components relative to landmarks from one or more teeth, or to generate appliance components based on landmarks from one or more teeth. Such landmarks may include a cross section of a tooth, a midpoint (geometric center of a cross section of a tooth), a gingival boundary, a closest point between two adjacent teeth (e.g., a point of contact between adjacent teeth or a point of closest approach (or closest proximity), a convex hull (polygon whose vertices include a subset of the vertices in a given set of vertices), a center of mass (midpoint, center point, centroid, or geometric center of the tooth), landmarks in the local coordinate system of one or more teeth or other landmarks. PCT Patent Application WO2021240290A1 (the entirety of which is incorporated herein by reference)

describes techniques to place appliance components relative to one or more teeth using neural networks, or to generate appliance components based on data from one or more teeth. A non-limiting list of neural networks which may be used in the placement or generation of appliance components includes: an encoder, a decoder, an autoencoder, a U-Net, a transformer, a multi-layer perceptron (MLP), a graph convolutional neutral network (GCNN), a generative adversarial network (GAN), a conditional generative adversarial network (cGAN), an encoder-decoder based CNN, a U-Net CNN, a GAN with a PatchGAN discriminator, and/or another deep neutral network (DNN). The place or generation of appliance components (or the validation thereof) may benefit from the computation of mesh element features, which may improve the ability of neural networks to understand the shape and/or structure of 3D oral care representations.

Systems and techniques of this disclosure may be trained to validate such appliance component placements or such appliance component generations. This digital representation of a dental restoration appliance may (e.g., described as a 3D mesh or 3D point cloud) may be sent to a 3D printer for fabrication. The physical dental restoration appliance may then be placed into the patient's mouth at the time of treatment, and be used to shape dental composite (e.g., a window in the appliance may be opened; dental composite may be injected into the opening; a door may be closed on the opening, creating a tight seal; a curing light such as an LED curing light may be applied to cure the dental composite in the shape produced by the internal contours of the appliance; the result is to form, cure and adhere veneers onto one or more teeth of the patient's dentition).

Techniques of this disclosure may, in some instances, be trained using federated learning. Federated learning may enable multiple remote clinicians to iteratively improve a machine learning model (e.g., validation of 3D oral care representations, mesh segmentation, mesh cleanup, other techniques which involve labeling mesh elements, coordinate system prediction, non-organic object placement on teeth, appliance component generation, tooth restoration design generation, techniques for placing 3D oral care representations, setups prediction, generation or modification of 3D oral care representations using autoencoders, generation or modification of 3D oral care representations using transformers, generation or modification of 3D oral care representations using diffusion models, 3D oral care representation classification, imputation of missing values), while protecting data privacy (e.g., the clinical data may not need to be sent "over the wire" to a third party). Data privacy is particularly important to clinical data, which is protected by applicable laws. A clinician may receive a copy of a machine learning model, use a local machine learning program to further train that ML model using locally available data from the local clinic, and then send the updated ML model back to the central hub or third party. The central hub or third party may integrate the updated ML models from multiple clinicians into a single updated ML model which benefits from the learnings of recently collected patient data at the various clinical sites. In this way, a new ML model may be trained which benefits from additional and updated patient data (possibly from multiple clinical sites), while those patient data are never actually sent to the 3rd party. Training on a local in-clinic device may, in some instances, be performed when the device is idle or otherwise be performed during off-hours (e.g., when patients are not being treated in the clinic). Devices in the clinical environment for the collection of data and/or the training of ML models for techniques described here may include intra-oral scanners, CT scanners, X-ray machines, laptop computers, servers, desktop computers or handheld devices (such as smart phones with image collection capability).

In addition to federated learning techniques, in some implementations, contrastive learning may be used to train, at least in part, the ML models described herein. Contrastive learning may, in some instances, augment samples in a training dataset to accentuate the differences in samples from difference classes and/or increase the similarity of samples of the same class.

FIG. 1 shows an example processing unit 102 that operates in accordance with the techniques of the disclosure. The processing unit 102 provides a hardware environment for the training of one or more of the neural networks described throughout the specification. In general, and as will be described in more detail elsewhere, training the one or more neural networks is done through the provision of one or more training datasets. As a result, the quality and makeup of the training dataset for a neural network can have a significant impact on any neural networks trained therefrom. Dataset filtering and outlier removal can be advantageously applied to the training of the neural networks for the various techniques of the present disclosure (e.g., mesh reconstruction autoencoder, mesh segmentation, mesh segmentation validation, coordinate system prediction, coordinate system validation, mesh cleanup, mesh cleanup validation, chairside intraoral dental scan validation, clear tray aligners (CTA) setups validation, bracket/attachment/hardware placement validation, generating a custom oral care appliance component, placing a custom oral care appliance component, the validation of custom oral care appliances (e.g., such as validating the shape or placement of a dental restoration appliance component), restoration design generation, restoration design generation validation, fixture model validation and CTA trimline validation, validation using autoencoders, and setups prediction).

In the depicted example, processing unit includes processing circuitry that may include one or more processors 104 and memory 106 that, in some examples, provide a computer platform for executing an operating system 116, which may be a real-time multitasking operating system, for instance, or other type of operating system. In turn, operating system 116 provides a multitasking operating environment for executing one or more software components such as applications or other training routines. Processors 104 are coupled to one or more I/O interfaces 114, which provide I/O interfaces for communicating with devices such as a keyboard, controllers, display devices, image capture devices, other computing systems, and the like. Moreover, the one or more I/O interfaces 114 may include one or more wired or wireless network interface controllers (NICs) for communicating with a network. Additionally, processors 104 may be coupled to electronic display 108.

In some examples, processors 104 and memory 106 may be separate, discrete components. In other examples, memory 106 may be on-chip memory collocated with processors 104 within a single integrated circuit. There may be multiple instances of processing circuitry (e.g., multiple processors 104 and/or memory 106) within processing unit 102 to facilitate executing applications and/or processes (including applications and/or processes pertaining to machine learning) in parallel. The multiple instances may be of the same type, e.g., a multiprocessor system or a multicore processor. The multiple instances may be of different types, e.g., a multicore processor with associated multiple graphics processor units (GPUs). In some examples, processor 104 may be implemented as one or more microprocessors, digital signal processors (DSPs), application specific integrated circuits (ASICs), field-programmable gate array (FPGAs), or equivalent discrete or integrated logic circuitry, or a combination of any of the foregoing devices or circuitry.

The architecture of processing unit 102 illustrated in FIG. 1 is shown for example purposes only. Processing unit 102 should not be limited to the illustrated example architecture. In other examples, processing unit 102 may be configured in a variety of ways. Processing unit 102 may be implemented as any suitable computing system, (e.g., at least one server computer, workstation, mainframe, appliance, cloud computing system, and/or other computing system) that may be capable of performing operations and/or functions described in accordance with at least one aspect of the present disclosure. As examples, processing unit 102 can represent a cloud computing system, server computer, desktop computer, server farm, and/or server cluster (or portion thereof). In other examples, processing unit 102 may represent or be implemented through at least one virtualized compute instance (e.g., virtual machines or containers) of a data center, cloud computing system, server farm, and/or server cluster. In some examples, processing unit 102 includes at least one computing device, each computing device having a memory 106 and at least one processor 104.

Storage units 134 may be configured to store information within processing unit 102 during operation (e.g., 3D geometries, transformations to be performed on the 3D geometries, and the like). Storage units 134 may include a computer-readable storage medium or computer-readable storage device. In some examples, storage units 134 include at least a short-term memory or a long-term memory. Storage units 134 may include, for example, random access memories (RAM), dynamic random-access memories (DRAM), static random-access memories (SRAM), magnetic discs, optical discs, flash memories, magnetic discs, optical discs, flash memories, or forms of electrically programmable memories (EPROM) or electrically erasable and programmable memories (EEPROM).

In some examples, storage units 134 are used to store program instructions for execution by processors 104. Storage units 134 may be used by software or applications running on processing unit 102 to store information during program execution and to store results of program execution. For instance, storage units 134 can store any number of neural networks 110*a*-110*n*, including those neural networks described herein. According to some implementations the neural networks 110*a*-110*n* can be trained neural networks according to techniques disclosed herein. In other implementations, one or more of the neural networks 110*a*-110*n* can be untrained or partially trained.

As will be described in more detail elsewhere, the ML models (e.g., one or more neural networks) may be trained in supervised and unsupervised manners. Supervised models which may be trained for making recommendations described herein include: regression model (such as linear regression), decision tree, random forest, boosting, Gaussian process, k-nearest neighbors (KNN), logistic regression, Naïve Bayes, gradient boosting algorithms (e.g., GBM, XGBoost, LightGBM and CatBoost), support vector machine (SVM), or a fully connected neural network model that has been trained for classification. In some cases, a multilayer perceptron (MLP) may be used to predict missing procedure parameters given the known procedure parameters.

Unsupervised models which may be trained for making recommendations described herein include: clustering techniques such as K-means clustering, density-based spatial clustering of applications with noise (DBSCAN), Gaussian mixture model, Balance Iterative Reducing and Clustering using Hierarchies (BIRCH), Affinity Propagation clustering, Mean-Shift clustering, Ordering Points to Identify the Clustering Structure (OPTICS), Agglomerative Hierarchy clustering, and spectral clustering.

Regardless of whether the training is supervised or unsupervised, there are multiple optimization approaches which can be used in the training of the neural networks of this disclosure (e.g., updating the neural network weights), including gradient descent (which determines a training gradient using first-order derivatives and is commonly used in the training of neural networks), Newton's method (which may make use of second derivatives in loss calculation to find better training directions than gradient descent, but may require calculations involving Hessian matrices), and conjugate gradient methods (which may have faster convergence than gradient descent, but do not require the Hessian matrix calculations which may be required by Newton's method). In some implementations, additional methods may be employed to update weights, in addition to or in place of the preceding methods. These additional methods include: the Levenberg-Marquardt method and simulated annealing. The backpropagation algorithm is used to transfer the results of loss calculation back into the network so that network weights can be adjusted, and learning can progress.

Neural networks contribute to the functioning of many of the applications of the present disclosure, including but not limited to: mesh reconstruction autoencoder, mesh segmentation, mesh segmentation validation, coordinate system prediction, coordinate system validation, mesh cleanup, mesh cleanup validation, chairside intraoral dental scan validation, clear tray aligners (CTA) setups validation, bracket/attachment/hardware placement validation, generating a custom oral care appliance component, placing a custom oral care appliance component, the validation of custom oral care appliances (e.g., such as validating the shape or placement of a dental restoration appliance component), restoration design generation, restoration design generation validation, fixture model validation and CTA trimline validation, and validation using autoencoders. The neural networks of the present disclosure may embody part or all of a variety of different neural network models. Examples include the U-Net architecture, multi-later perceptron (MLP), transformer, pyramid architecture, recurrent neural network (RNN), autoencoder, variational autoencoder, regularized autoencoder, conditional autoencoder, capsule network, capsule autoencoder, stacked capsule autoencoder, denoising autoencoder, sparse autoencoder, conditional autoencoder, long/short term memory (LSTM), gated recurrent unit (GRU), deep belief network (DBN), deep convolutional network (DCN), deep convolutional inverse graphics network (DCIGN), liquid state machine (LSM), extreme learning machine (ELM), echo state network (ESN), deep residual network (DRN), Kohonen network (KN), neural Turing machine (NTM), and generative adversarial network (GAN). In some implementations, an encoder structure or a decoder structure may be used. Each of these models has its own particular advantages. A particular model may be especially well suited to one or another model.

In some implementations, the neural networks of this disclosure can be adapted to operate on 3D point cloud data (alternatively on 3D meshes or 3D voxelized representations). Numerous neural network implementations may be applied to the processing of 3D representations and may be applied to training predictive and/or generative models for oral care applications, including: PointNet, PointNet++, SO-Net, spherical convolutions, Monte Carlo convolutions and dynamic graph networks, PointCNN, ResNet, MeshNet, DGCNN, VoxNet, 3D-ShapeNets, Kd-Net, Point GCN, Grid-GCN, KCNet, PD-Flow, PU-Flow, MeshCNN and DSG-Net. Oral care applications include, but are not limited to: mesh reconstruction autoencoder, mesh segmentation, mesh segmentation validation, coordinate system prediction, coordinate system validation, mesh cleanup, mesh cleanup validation, chairside intraoral dental scan validation, clear tray aligners (CTA) setups validation, bracket/attachment/hardware placement validation, generating a custom oral care appliance component, placing a custom oral care appliance component, the validation of custom oral care appliances (e.g., such as validating the shape or placement of a dental restoration appliance component), restoration design generation, restoration design generation validation, fixture model validation and CTA trimline validation, validation using autoencoders, setups prediction, and generating dental restoration appliances.

Some of the techniques of this disclosure may use an autoencoder, in some implementations. Possible autoencoders include but are not limited to: AtlasNet, FoldingNet and 3D-PointCapsNet. Some autoencoders may be implemented, at least in part, based on PointNet.

Some techniques of this disclosure relate to hardware placement. ML models directed thereto may be enhanced using representation learning. For instance, representation learning can involve training a first neural network to learn a representation of the teeth and the same or a second neural network to learn a representation of the hardware, and then using a third neural network to generate transforms for the hardware to place the hardware on the teeth. In other implementations, one or more appliance components may be placed relative to one or more teeth. Some implementations may use a U-Net to generate a representation. Some implementations may use an autoencoder, such as a VAE or a Capsule Autoencoder to learn a representation of the essential characteristics of the one or more meshes related to the oral care domain (including, in some instances, information about the structures of the tooth meshes). Then that representation may be used (either a latent vector or a latent capsule) as input to a module which generates the one or more transforms for the one or more hardware elements or appliance components. These transforms may in some implementations place the hardware elements or appliance components into poses required for appliance generation (e.g., dental restoration appliances or indirect bonding trays). In some implementations, a transform may be described by a 9×1 transformation vector (e.g., that specifies a translation vector and a quaternion). In other implementations, a transform may be described by a transformation matrix (e.g., a 4×4 affine transformation matrix). In some implementations, a principal components analysis may be performed on an oral care mesh, and the resulting principal components may be used as at least a portion of the representation of the oral care mesh in later machine learning and/or other predictive or generative processing.

Additional approaches may also be used to improve the performance of the ML models, according to particular implementations. For instance, end-to-end training may be applied to the techniques of the present disclosure which involves two or more neural networks, where the two or more neural networks are trained together (e.g., the weights are updated concurrently during the processing of each batch of input oral care data). End-to-end training may, in some implementations, be applied to hardware/component placement by concurrently training a neural network which learns a representation of one or more oral care objects, along with a neural network which may process those representations.

Another approach to improve the ML models described herein is the use of transfer learning. In some implementations, a network (e.g., a U-Net) may be trained on a first task (e.g., such as coordinate system prediction), and then be used to provide one or more of the starting neural network weights for the training of another neural network, which is trained to perform a second task (e.g., setups prediction). The first network may learn the low-level neural network features of oral care meshes and be shown to work well at the first task. The second network may experience faster training and/or improved performance by using the first network as a starting point in training. Certain layers may be trained to encode neural network features for the oral care meshes that were in the training dataset. These layers may thereafter be fixed (or receive minor tweaks over the course of training) and be combined with other neural network components, such as additional layers, which are trained for one or more oral care tasks. In this fashion, a portion of a neural network for one or more of the techniques of the present disclosure may receive initial training on another task, which may yield important learning in the trained network layers. This encoded learning may then be built-upon with further task-specific training. In some implementations, a neural network for making predictions based on oral care meshes may first be partially trained on one or more generic/publicly available datasets before being further trained on oral care data.

In some implementations, a neural network which was previously trained on a first dataset (either oral care data or other data) and may subsequently receive further training on oral care data and be applied to oral care applications (such as a mesh reconstruction autoencoder, mesh segmentation, mesh segmentation validation, coordinate system prediction, coordinate system validation, mesh cleanup, mesh cleanup validation, chairside intraoral dental scan validation, clear tray aligners (CTA) setups validation, bracket/attachment/hardware placement validation, generating a custom oral care appliance component, placing a custom oral care appliance component, the validation of custom oral care appliances or components (e.g., such as validating the shape or placement of a dental restoration appliance component), restoration design generation, restoration design generation validation, fixture model validation and CTA trimline validation and validation using autoencoders). Transfer learning maybe employed to further train any of the following networks from the published literature: GCN (Graph Convolutional Networks), PointNet, ResNet or any of the other neural networks from the published literature which are listed earlier in this section.

And yet another approach involves adding attention gates to the ML models. In general, attention gates can be integrated with one or more of the neural networks of this disclosure, with the advantage of enabling an associated neural network architecture to focus attention on one or more input values. In some implementations, an attention gate may be integrated with a U-Net architecture, with the advantage of enabling the U-Net to focus on certain inputs. An attention gate may also be integrated with an encoder or with an autoencoder (such as VAE or capsule autoencoder). Some implementations of the techniques of the present disclosure may benefit from one or more attention layers in a transformer, where a transformer is trained to generated 3D oral care representations.

Figure 2:
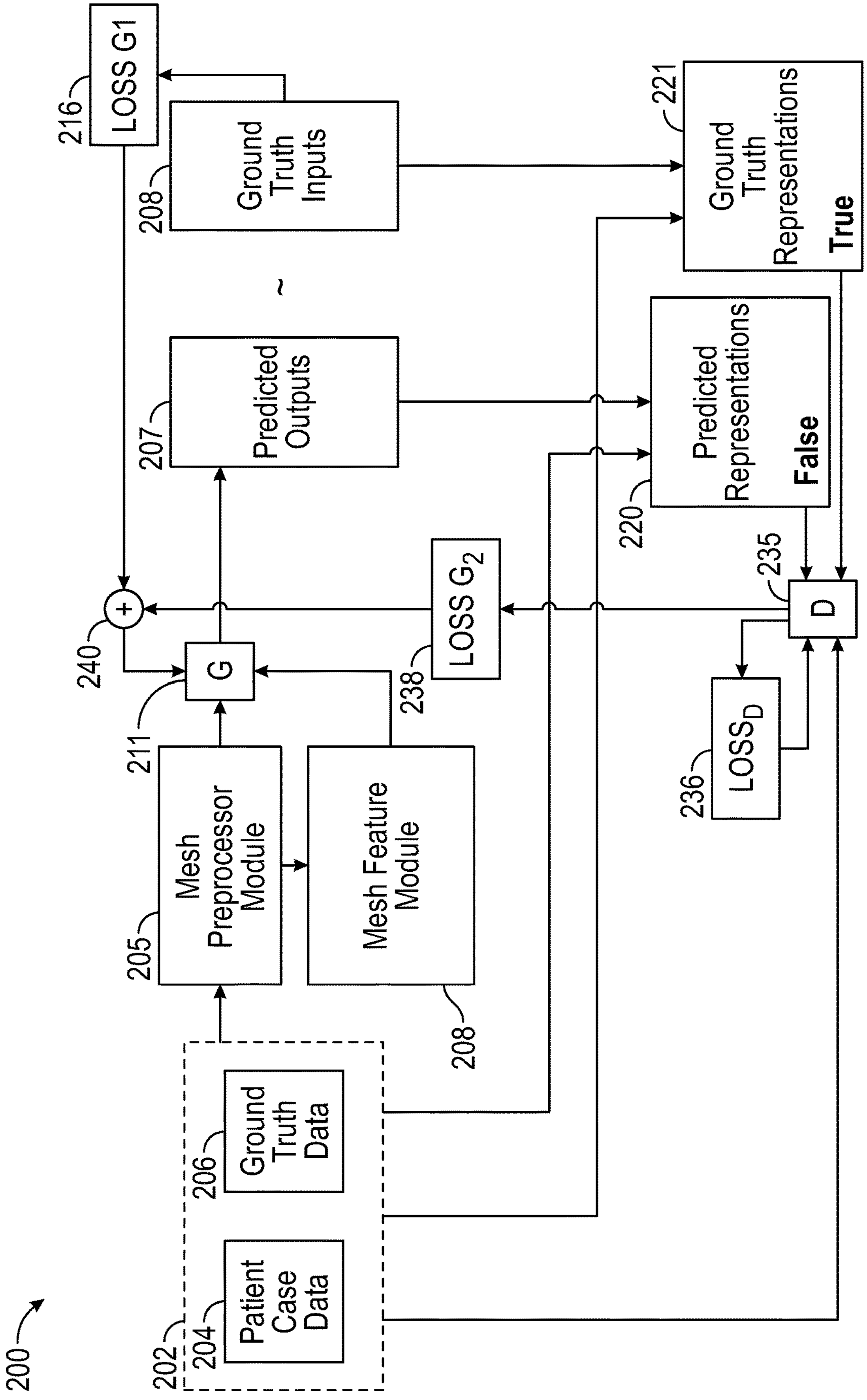
FIG. 2 shows an example generalized technique for training a generator or other neural network according to various aspects of this disclosure.

FIG. 2 is an example technique 200 that can be used to train ML models described herein. In general, receiving module 202 is configured to receive patient case data 204. Typically, the patient case data 204 represents a digital representation of the patient's mouth. This can mean, for example, that the receiving module 202 can receive one or more malocclusion arches (e.g., a 3D meshes that represent the upper and lower arches of the patient's teeth, i.e., a dentition of the patient's mouth that includes multiple aspects of the patient's dental anatomy, which may include teeth, and which may include gums). According to particular implementations, malocclusion arches can be arranged in a bite position or other orientation. In other implementations, one a single arch may be necessary. For illustrative purposes, additional implementations are described in more detail below. Stated differently, the receiving module 202 can receive mesh data corresponding to 3D meshes of dentitions for one or more patients. It should be appreciated that both the amount of 3D mesh data and the type of 3D mesh data received by receiving module 202 as part of the patient case data can differ based on specific implementations. For instance, in implementations concerning validation of bracket placement, the mesh data received as part of the patient case data 204 may only include 3D mesh data concerning specific teeth and associated brackets, whereas in implementations concerning the validation of 3D printed parts, the 3D data received as part of the patient case data 204 may include 3D mesh data related to the part being examined in the form of a CT scan, or other diagnostic imagery, to name a few additional examples. Patient case data 204 may also include 3D representations of the patient's gingival tissue, according to particular implementations.

As shown in the example, the receiving module 202 also receives "ground truth" data 206. In general, these "ground truth" data 206 specify an expected result of applying other techniques disclosed herein, be it mesh segmentation, coordinate system prediction, mesh cleanup, restoration design, and bracket/attachment placement, and all of the validation applications of the disclosure, to name a few examples. Used herein, "ground truth" and "reference" will be used interchangeably. For instance, it should be appreciated the "reference" transformation vectors are equivalent to "ground truth" transformation vectors for the purposes of this disclosure. According to particular implementations, and as will be described in more detail below, that "ground truth" data 206 can include "ground truth" one-hot vectors that describe an expected transformation of the 3D geometry. As another example, "ground truth" data 206 can include expected labels for aspects of the 3D geometry. Other examples are also provided below. According to particular implementations, the "ground truth" data 206 can be predefined or provided as a result of the outcome of performing one or more other techniques disclosed herein.

According to particular implementations the receiving module 202 can also be configured to perform data augmentation on one or more aspects of the received data, including patient data 204 and "ground truth" data 206. Data augmentation is described in more detail below.

The system 100 can be configured to provide each mesh received by the receiving module 202 to mesh preprocessor module 205, allowing any 3D mesh data received in the patient case data 206 to be pre-processed. This pre-processing step allows the system to convert the mesh into a form that allows the input mesh to be "consumed" by a neural network, or other ML technique. In one implementation, the mesh preprocessor module 205 can be configured to generate a combination of edge, vertex, and face lists. One or more of these generated lists can be provided to both the generator 211, and mesh feature module 208, described in more detail below.

In addition to utilizing the mesh preprocessor module 205, system 100 can perform a number of additional operations, both before and after providing patient case data 204 to the mesh preprocessor module 205. For instance, according to particular implementations, the system 100 can perform mesh cleanup on the patient case data 204 before providing the patient case data 204 to the mesh preprocessor module 205. Additionally, system 100 may resample or update any of the information generated by the mesh preprocessor module 205. For instance, in implementations where the mesh preprocessor module 205 generates a combination of edge, vertex, and face lists, the system can resample, update, or otherwise modify the labels identified in those lists. Additionally, the system 100 can perform data augmentation of resampled data, according to particular implementations.

The mesh feature module 208 can be configured to receive the lists generated by the mesh preprocessor module 205 and generate feature information related thereto that can be used by an ML model to produce a prediction. For instance, in one implementation, the mesh feature module 208 can compute one or more of: edge midpoints, edge curvatures, edge normal vectors, edge normalization vectors, edge movement vectors, and other information pertaining to each tooth in the 3D meshes received by receiving module 202. According to particular implementations, mesh feature module 208 may or may not be utilized. That is, it should be appreciated that the computation of any of the edge midpoints, edge curvatures, edge normal vectors, and edge movement vectors for the 3D mesh data including the in the patient data 206 is optional. One advantage of using the mesh feature module 208 is that a system utilizing mesh feature module 208 can be trained more quickly and accurately, but the technique 200 nevertheless performs better than existing techniques without the use of the mesh feature module 208.

Technique 200 also leverages a generative adversarial network ("GAN") to achieve certain aspects of the improvements. In general, a GAN is an ML model where two neural networks "compete" against each other to provide predictions, these predictions are evaluated, and the evaluations of the two models are used to improve the training of each other. In some implementations, the GAN can be a conditional GAN where the generated outputs are conditioned on some input data. One example where conditional GANs have been found to provide benefits is in the domain of restorative design. In those implementations, these conditioned input data can be unrestored meshes and the associated text prescriptions. In some implementations, and as will be described below, the text prescriptions may be processing using natural language processing (NLP) to extract key values, such as the additive height or the additive width that has been prescribed for each treated tooth (e.g., in the example of dental restoration design, which produces the target geometry for each treated tooth).

As shown in the instant example, the two neural networks of the GAN are a generator 211 and a discriminator 235. In other implementations, a model other than a neural network may be used for either a generator or a discriminator.

Generator 211 receives input (e.g., one or more of 3D meshes included in the patient case data 206). The generator 211 uses the received input to determine predicted outputs 207 pertaining to the 3D meshes, according to particular implementations. For instance, for segmentation, the generator 211 may be configured to predict segmentation labels, whereas in implementations where clear tray aligner setups are predicted, the predictions may include one or more vectors corresponding to one or more transformations to apply to the 3D mesh(es) included in the patient case data 206. Other predicted outputs 207 are also possible. In some implementations, the generator 211 may also receive random noise, which can include garbage data or other information that can be used to purposefully attempt to confuse the generator 211. According to particular implementations, and as described above, the generator 211 can implement any number of neural networks, including a MeshCNN, ResNet, a U-Net, and a DenseNet. In other instances, the generator may implement an encoder.

Because the generator 211 can be implemented as one or more neural networks, the generator 211 may contain an activation function. An activation function decides whether a neuron in a neural network will fire (e.g., send output to the next layer). Some activation functions may include: binary step functions, and linear activation functions. Other activation functions impart non-linear behavior to the network, including: sigmoid/logistic activation functions, Tanh (hyperbolic tangent) functions, rectified linear units (ReLU), leaky ReLU functions, parametric ReLU functions, exponential linear units (ELU), softmax function, swish function, Gaussian error linear unit (GELU), and scaled exponential linear unit (SELU). A linear activation function may be well suited to some regression applications (among other applications), in an output layer. A sigmoid/logistic activation function may be well suited to some binary classification applications (among other applications), in an output layer. A softmax activation function may be well suited to some multiclass classification applications (among other applications), in an output layer. A sigmoid activation function may be well suited to some multilabel classification applications (among other applications), in an output layer. A ReLU activation function may be well suited in some convolutional neural network (CNN) applications (among other applications), in a hidden layer. A Tanh and/or sigmoid activation function may be well suited in some recurrent neural network (RNN) applications (among other applications), for example, in a hidden layer.

After the generator 211 determines one or more predicted outputs 207, the generator 211 can be trained. In general, training the generator 211 involves comparing the predicted outputs 207 against respective ground truth inputs 208. For instance, the predicted output 207 pertaining to the lower left canine tooth corresponding to number twenty-seven of the Universal tooth number system would be compared with the ground truth output 208 for the same canine tooth. As previously mentioned, a ground truth input is an input that has been verified as the correct label for a particular portion of the 3D mesh data included in the patient case data 206. According to particular implementations, the ground truth inputs 208 can be derived or otherwise determined from the ground truth data 206 or may be the ground truth data 206.

The difference between the predicted outputs 207 and the ground truth inputs 208 can be used to compute one or more loss values G1 216. For example, the differences can be used as part of a computation of a loss function or for the computation of a reconstruction error. Some implementations may involve a comparison of the volume and/or area of the two meshes (that is representations 207 and 208). Some implementations may involve the computation of a minimum distance between corresponding vertices/faces/edges/voxels of two meshes. For a point in one mesh (vertex point, midpoint on edge, or triangle center, for example) compute the minimum distance between that point and the corresponding point in the other mesh. In the case that the other mesh has a different number of elements or there is otherwise no clear mapping between corresponding points for the two meshes, different approaches can be considered.

Regardless of the manner in which differences are determined between predicted outputs 207 and ground truth inputs, various loss values can be determined as part of technique 200 or any other technique described herein. These losses include L1 loss, L2 loss, MSE loss, cross entropy loss, among others. Losses may be computed and used in the training of neural networks, such as multi-layer perceptron's (MLP), U-Net structures, generators and discriminators (e.g., for GANs), autoencoders, variational autoencoders, regularized autoencoders, masked autoencoders, transformer structures, or the like. Some implementations may use either triplet loss or contrastive loss, for example, in the learning of sequences.

Losses may also be used to train encoder structures and decoder structures. A KL-Divergence loss may be used, at least in part, to train one or more of the neural networks of the present disclosure, such as a mesh reconstruction autoencoder, with the advantage of imparting Gaussian behavior to the optimization space. This Gaussian behavior may enable a reconstruction autoencoder to produce a better reconstruction (i.e., when a latent vector representation is modified and that modified latent vector is reconstructed using a decoder, the resulting reconstruction is more likely to be a valid instance of the inputted representation). There are other techniques for computing losses which may be described elsewhere in this disclosure. Such losses may be based on quantifying the difference between two or more 3D representations.

Mean squared error (MSE) loss may involve the calculation of an average squared distance between two sets, vectors or datasets. MSE may be generally minimized. MSE may be applicable to a regression problem, where the prediction generated by the neural network or other ML model may be a real number. In some implementations, a neural network may be equipped with one or more linear activation units on the output to generate an MSE prediction. Mean absolute error (MAE) loss and mean absolute percentage error (MAPE) loss are also possibilities.

Cross entropy may, in some implementations, be used to quantify the difference between two or more distributions. Cross entropy loss may, in some implementations, be used to train the neural networks of the present disclosure. Cross entropy loss may, in some implementations, involve comparing a predicted probability to a ground truth probability. Other names of cross entropy loss include “logarithmic loss,” “logistic loss,” and “log loss”. A small cross entropy loss may indicate a better (i.e., more accurate) model. Cross entropy loss may be logarithmic. Cross entropy loss may, in some implementations, be applied to binary classification problems. In some implementations, a neural network may be equipped with a sigmoid activation unit at the output to generate a probability prediction. In the case of multi-class classifications, cross entropy may also be used. In such a case, a neural network which has been trained to make multi-class predictions may, in some implementations, be equipped with one or more softmax activation functions at the output (e.g., where there is one output node for class that is to be predicted).

Other loss calculation techniques which may be applied in the training of the neural networks of this disclosure include one or more of: Huber loss, Hinge loss, Categorical hinge loss, cosine similarity, Poisson loss, Logcosh loss, or mean squared logarithmic error loss (MSLE). Other loss calculation methods are described herein and may be applied to the training of any of the neural networks described in the present disclosure.

One or more of the neural networks of the present disclosure may, in some implementations, be trained, at least in part by a loss which is based on at least one of: a Point-wise Mesh Euclidean Distance (PMD) and an Earth Mover's Distance (EMD). Some implementations may incorporate a Hausdorff Distance (HD) calculation into the loss calculation. Computing the Hausdorff distance between two or more 3D representations (such as 3D meshes) may provide one or more technical improvements, in that the HD not only accounts for the distances between two meshes, but also accounts for the way that those meshes are oriented, and the relationship between the mesh shapes in those orientations (or positions or poses). Hausdorff distance may improve the comparison of two or more tooth meshes, such as two or more instances of a tooth mesh which are in different poses (e.g., such as the comparison of predicted setup to ground truth setup which may be performed in the course of computing a loss value for training a setups prediction neural network).

Referring again to FIG. 2, G1 216 can represent a regression loss between the predicted outputs 207 and the ground truth inputs 208. That is, according to one implementation, loss G1 216 reflects a percentage by which predicted outputs 207 deviate from the ground truth inputs 208. That said, generator loss G1 216 can be an L2 loss, a smooth L1 loss, or some other kind of loss. According to particular implementations, an L1 loss is defined as $$L1 = \sum_{i=0}^{n} |P_i - G_i|,$$

where P represents the predicted outputs 207 and G represents the ground truth inputs 208. According to particular implementations, an L2 loss can be defined as $$L2 = \sum_{i=0}^{n} (P_i - G_i)^2,$$

again where P represents the predicted outputs 207 and G represents the ground truth inputs 208. In addition, and as will be described in more detail below, the loss values G1 216 can be provided to the generator 211 to further train the generator 211, e.g., by modifying one or more weights in the generator 211's neural network to train the underlying model and improve the model's ability to generate predicted outputs 207 that mirror or substantially mirror the ground truth inputs 208. Any of these losses can be used to supply a loss value for use in training a neural network by way of a suitable training algorithm, such as backpropagation. In some instances, an accuracy score may be used in the training of a neural network. The accuracy score quantifies the difference between a predicted data structure and a ground truth data structure. The accuracy score (e.g., in normalized form) may be fed back into the neural network in the course of training the network, for example, through backpropagation. In the case of segmentation, an accuracy score may count matching labels between a predicted and a ground truth mesh (i.e., where each mesh element has an associated label). The higher the percentage of matching labels, the better the prediction (i.e., when comparing predicted labels to ground truth labels). A similar accuracy score may be computed in the case of mesh cleanup, which also predicts labels for mesh elements. The number or percentage of matches between the predicted labels and the ground truth labels can be used as an accuracy score which may be used to train the neural network which drives mesh cleanup (i.e., the accuracy score may be normalized).

Additionally, according to particular implementations, the system 100 can use predicted outputs 207 to generate predicted representations 220. Furthermore, the system 100 can use the ground truth inputs 208 to generate ground truth representations 211. For example, in an implementation pertaining to clear tray aligner generation, the predicated transformations and the ground truth transformations can be applied to the patient case data 206 to generate predicted transformations and ground truth transformations of the patient case data 206.

According to particular implementations, the predicted representations 220 and ground truth representations 211 can be flagged or otherwise annotated to indicate whether the representation corresponds to ground truth data 206. Furthermore, according to particular implementations, representation 220 can be assigned a value of "false" to indicate that the representation does not correspond to the ground truth labels 208, while representation 221 can be assigned a value of "true."

According to particular implementations, the representations 220 and 221 are provided as inputs to the discriminator 235. In addition, according to particular implementations, 3D mesh data in the patient case data 206 is also provided to the discriminator 235. That is, the discriminator 235 can receive various representations of the data corresponding to patient case data 206, the predicted outputs 207, ground truth data 206, ground truth inputs 208, and the representations 220 and 221. In general, the discriminator 235 is configured to determine when an input is generated from the predicated outputs 207 or when an input is generated from the ground truth inputs 208. Outputs of the discriminator 235 are described in more detail in connection to implementations discussed herein.

The discriminator 235 can be initially trained in a variety of ways. For instance, the discriminator 235 can be configured as an encoder structure, which in some situations, such as the ones described herein, can be configured to perform validation when used as a generator. For instance, the initial encoder included in the discriminator 235 can be configured with random edge weights. Using backpropagation, the encoder—and thereby the discriminator 235—can be successively refined by modifying the values of the weights to allow the discriminator 235 to more accurately determine which inputs should be identified as "true" ground truth representations and which inputs should be identified as "false" ground truth representations. In other words, while the discriminator 235 can be initially trained, the discriminator 235 continues to evolve/be trained as technique 200 is performed. And like generator 211, with each execution of technique 200 the accuracy of the discriminator 235 improves. Although as understood by a person of ordinary skill in the art the improvements to the discriminator 235 will reach a limit by which the discriminator 235's accuracy does not statistically improve, at which time the discriminator 235's training is considered complete. Stated differently, when the discriminator 235 has trouble distinguishing between predicted representations 220 and ground truth representations 221, the system 100 can consider the training of both the generator 211 and discriminator 235 to be complete. Used herein, when the training of the generator 211 and the discriminator 235 is complete, they are described as being fully trained.

After the discriminator 235 generates an output, the technique 200 then compares the output of the discriminator 235 against the input to determine whether the discriminator 235 accurately distinguished between the predicted representation 220 and ground truth representation 221. For instance, the output of the discriminator 235 can be compared against the annotation of the representation. If the output and annotation match, then the discriminator 235 accurately predicted the type of input that the discriminator 235 received. Conversely, if the output and annotation do not match, then the discriminator 235 did not accurately predict the type of input that the discriminator 235 received. In some implementations, and like the generator 211, the discriminator 235 may also receive random noise, purposefully attempting to confuse the discriminator 235.

In addition, and according to particular implementations, the discriminator 235 may generate additional values that can be used to train aspects of the system implementing technique 200. In one example, the discriminator 235 may generate a discriminator loss value 236, which reflects how accurately the discriminator 235 determined whether the inputs corresponded to the predicted representation 220 and/or ground truth representation 221. According to particular implementations, the discriminator loss 236 is larger when the discriminator 235 is less accurate and smaller when the discriminator 235 is more accurate in its predictions. In another example, the discriminator 235 may generate a generator loss value G2 238. According to particular implementations, while not directly inverse to discriminator loss 236, generator loss value G2 238 generally exhibits an inverse relationship to discriminator loss 236. That is, when discriminator loss 236 is large, generator loss G2 238 is small and when discriminator loss 236 is small, generator loss G2 238 is large. In some implementations, discriminator loss 236 may be determined using a binary cross entropy loss function that is calculated for both "true" and "false" models. In some implementations, generator loss may be composed of two losses: 1) the first loss is the generator loss G2 238 as determined by the discriminator (hence a binary cross entropy may be used); and 2) the second loss may be implemented by an l1-norm or mean square error that measures the difference between the desired output and the actual output of the generator 211, e.g., as specified by generator loss G1 216.

In other words, and as illustrated in FIG. 2, generator loss G2 238 can be added to generator loss G1 216 using a summation operation 240. And the summed value of generator loss G1 216 and G2 238 can be provided to generator 211 for the purposes of training generator 211. That said, it should be appreciated that the computation of the generator loss G1 216 is not necessary to the training of the GAN shown in FIG. 2. In some implementations, it may be possible to train either the generator 211 or the discriminator 235 using only a combination of generator loss G2 238 and discriminator loss 236. But like other optional aspects of this disclosure, using the generation loss G1 216 can be utilized to more quickly train the discriminator 235 to produce more accurate predictions. The system 100 may use other steps or operations as part of the described technique, according to particular implementations. For instance, as already described, but not depicted, implementations pertaining to clear tray aligner setups may use one or more transformation steps to transform patient data 206 using predicted outputs 207 and ground truth inputs 208 that correspond to one or more 3D mesh transformations (e.g., scaling, rotation, and/or translation operations).

According to particular implementations loss G1 216 and loss G2 238 can also include one or more inference metrics that specify one or more differences between predicted outputs 207 and ground truth inputs 208 and/or predicted representations 202 and ground truth representations 221. That is, an optional step, system 100 may generate these inference metrics to further refine the training of one or more neural networks or ML models. These inference metrics may include: an intersection over union metric, an average boundary distance metric, a boundary percentage metric, and an over-segmentation ratio, to name a few examples.

In general, the intersection over union metric specifies the percentage of correctly predicted edges, faces, and vertices within the mesh, after an operation, such as segmentation is complete. The average boundary distance specifies the distance between the predicted outputs 207 (or the predicted representations 220) and the ground truth inputs 208 (or the ground truth representations 221) for a 3D representation, such as a 3D mesh. The boundary percentage specifies the percentage of mesh boundary length of a 3D mesh, such as a segmented 3D mesh, where the distance between ground truth inputs 208 (or the ground truth representations) and predicted outputs 207 (or the predicted representations 220) is below a threshold. For instance, the threshold can determine whether one or more predicted outputs 207, such as a small line segment between each pair of boundary points, is close enough to the ground-truth input 208. Where technique 200 is used to implement a segmentation process, if the distance is below the threshold the system 100 can label the particular line segment as a perfect boundary segment. The percentage represents a ratio of segments which reside within the predicted boundary compared to the ground-truth boundary. And the over-segmentation ratio specifies the percentage of the length of the boundaries that the tooth is over-segmented, according to particular implementations, the one or more inference metrics can be used to additionally train the generator 211 or the discriminator 235, or both.

The techniques of this disclosure may include operations such as 3D convolution, 3D pooling, 3D un-convolution and 3D un-pooling. 3D convolution may aid segmentation processing, for example in down sampling a 3D representation (such as a 3D mesh or point cloud). 3D un-convolution undoes 3D convolution, for example, in a U-Net. 3D pooling may aid the segmentation processing, for example in summarized neural network feature maps. 3D un-pooling undoes 3D pooling, for example in a U-Net. These operations may be implemented by way of one or more layers in the predictive or generative neural networks described herein. These operations may be applied directly on aspects of the 3D representation such as mesh elements, which may include mesh edges or mesh faces. These operations provide for technical improvements over other approaches because the operations are invariant to mesh rotation, scale, and translation changes. In general, these operations depend on edge (or face) connectivity, therefore these operations remain invariant to mesh changes in 3D space as long as edge (or face) connectivity is preserved. That is, the operations may be applied to an oral care mesh and produce the same output regardless of the orientation, position or scale of that oral care mesh, which may lead to data precision improvement. MeshCNN is a general-purpose deep neural network library for 3D triangular meshes, which can be used for tasks such as 3D shape classification or mesh element labelling (e.g., for segmentation or mesh cleanup). MeshCNN implements these operations on mesh edges. Other toolkits and implementations may operate on edges or faces.

Technique 200 can be used to train ML models for many digital dentistry and digital orthodontics applications. Table 2 illustrates how technique 200 can receive different data 204 and 206 for certain digital dentistry applications, as well as a form that the predicted outputs 207 may take according to particular implementations.

ML models, such as those described herein, may be trained to generate transforms to place prefabricated components (e.g., from a library of components) for use in creating a dental restoration appliance. Such a dental restoration appliance may be used to shape dental composite in the patient's mouth while that composite is cured (e.g., using a curing light), to ultimately produce veneers on one or more of the patient's teeth. The 3M FILTEK Matrix is an example of such a product. Dental restoration appliance components (e.g., library components) which may be placed using the techniques of this disclosure include: vents (e.g., which may allow composite material to flow out of the appliance), rear snap clamps (e.g., which may enable the appliance to be grasped or handled) door hinges (e.g., which may enable doors to swivel open or closed), door snaps (e.g., which may secure doors in a closed position), an incisal registration feature (e.g., which may assist in appliance alignment), center clips (e.g., which may enable an appliance to be aligned), custom labels, a manufacturing case frame, a diastema matrix handle, among others. Further details about placed features and generated features may be found in PCT patent application WO2021/240290A1, the entirety of which is incorporated herein by reference.

TABLE 2

| Digital Dentistry Application | Patient Data 204 | Ground Truth Data 206 | Predicted Outputs 207 | Representations 220 and 221 |
|---|---|---|---|---|
| Mesh segmentation | One or more post-cleanup dental arches | Element labels (e.g., edge, vertex, and face elements) | Element labels (e.g., edge, vertex, and face elements) | One or more arches with labeled elements |
| Coordinate system generation | One or more segmented teeth and one or more transformations that describe a coordinate system relative to each of the one or more teeth | One or more transformations that describe a coordinate system relative to each of the one or more teeth | One or more transformations that describe a coordinate system for each tooth in the patient data 204 | The one or more segmented teeth transformed by the one or more transformations |
| Mesh cleanup | One or more dental arches prior to clean-up | Element labels (e.g., edge, vertex, and face elements) | Element labels (e.g., edge, vertex, and face elements) | Arch with labeled elements |
| Appliance component placement | One or more (e.g., Full arch of) segmented teeth and a digital representation of one or more library components | One or more transformations that define a position of the digital representation of the library component(s) | One or more transformations that define a position of the digital representation of the library component(s) | The library component(s) positioned in the arch as specified by the one or more transformations |
| Bracket, attachment and/or other hardware placement | One or more teeth, one or more brackets or attachments (or other hardware) for respective ones of the one or more teeth | One or more transformations that define a position of the one or more brackets or attachments (or other hardware) | One or more transformations that define a position of the one or more brackets or attachments (or other hardware) | The bracket or attachment (or other hardware) positioned in the arch as specified by the one or more transformations |
| Dental restoration appliance component generation | One or more segmented teeth (e.g., comprising one or both arches) | 3D representation (e.g., 3D mesh) of an appliance component that is known to be correctly formed | 3D representation (e.g., 3D mesh) of an appliance component (e.g., a mold parting surface) | 3D representation (e.g., 3D mesh) of an appliance component (e.g., a mold parting surface) |
| Dental restoration generation | A first representation that defines an unrestored state of the patient's dentition, including an unrestored state of the patient's teeth | Data pertaining to an outcome of the dental restoration | A digital representation that defines a restored state for the first digital representation based on the data pertaining to the outcome of the dental restoration | A restored state for the first digital representation |

For instance, in segmentation implementations, each patient case in that dataset 204 consists of a pre-segmented arch of teeth. In some implementations, the technique 200 can be used to segment each tooth in the arch, and labels that tooth with its identity (i.e., perform traditional tooth segmentation). In some implementations, the technique 200 can be used to separate the facial and the lingual portions of the arch (i.e., perform facial-lingual segmentation). In some implementations, the technique 200 can be used to separate the gingival portions of the arch from the teeth (i.e., perform teeth gums segmentation). In some implementations, the technique can be used to directly segment extraneous material away from the gingiva (i.e., perform trimline segmentation). Some segmentation implementations may use a MeshCNN to predict mesh element labels. Some implementations may train a U-Net structure to generate a representation of a 3D mesh and may also be trained to concurrently to predict mesh element labels. Still other implementations may use other models to predicts mesh element labels.

As discussed elsewhere in the specification, receiving module 202 receives patient case data. In the depicted example, receiving module 202 can receive patient case data 204 that includes dental arch data after one or more mesh clean-up operations have been performed on 3D arch geometry of a patient. For instance, this can result in one or more cleaned-up arch geometries, to name one example. Mesh cleanup operations may use one or more of: MeshCNN, U-Net or other models to predict mesh element labels.

According to particular implementations, 3D arch geometry may include 3D mesh geometry for a patient's gingival tissue, while in other implementations, 3D arch geometry may omit 3D arch geometry for a patient's gingival tissue. Furthermore, receiving module 202 can be configured to also receive ground truth labels as the ground truth labels 206, which describe verified or otherwise known to be accurate labels for the mesh elements (e.g., the labels "correct" and "incorrect") related to the segmented results performed on the 3D geometries. According to particular implementations, the labels described in relation to segmentation operations are used to specify a particular collection of mesh elements (such as an "edge" element, "face" element, "vertex" element, and the like) for a particular aspect of the 3D geometry. For instance, a single triangle polygon of a 3D mesh includes 3 edge elements, 3 vertex elements, and 1 face element. Therefore, it should be appreciated that a segmented tooth geometry consisting of many polygons can have a large number of labels associated with the segmented tooth geometry.

Additionally, the received geometries can have one or more labels applied to the respective geometries to generate representations 220 and 221. For instance, in one implementation, at each iteration of the generator 211, the generator 211 can output a label for each mesh element found in the input arch. Each of these labels flags the corresponding mesh element (e.g., an edge) as belonging to the gingival or tooth structures in the input mesh. In the case that the mesh element belongs to a tooth, the identity of that tooth is also specified. For example, one edge may be given a label to indicate that the mesh element belongs to the gingiva. Another mesh element may be given a label to indicate that the mesh element belongs to an upper right $3^{rd}$ molar. Still another mesh element may be given a label to indicate that the mesh element belongs to a lower left center incisor. And other labels are also possible.

Figure 3:
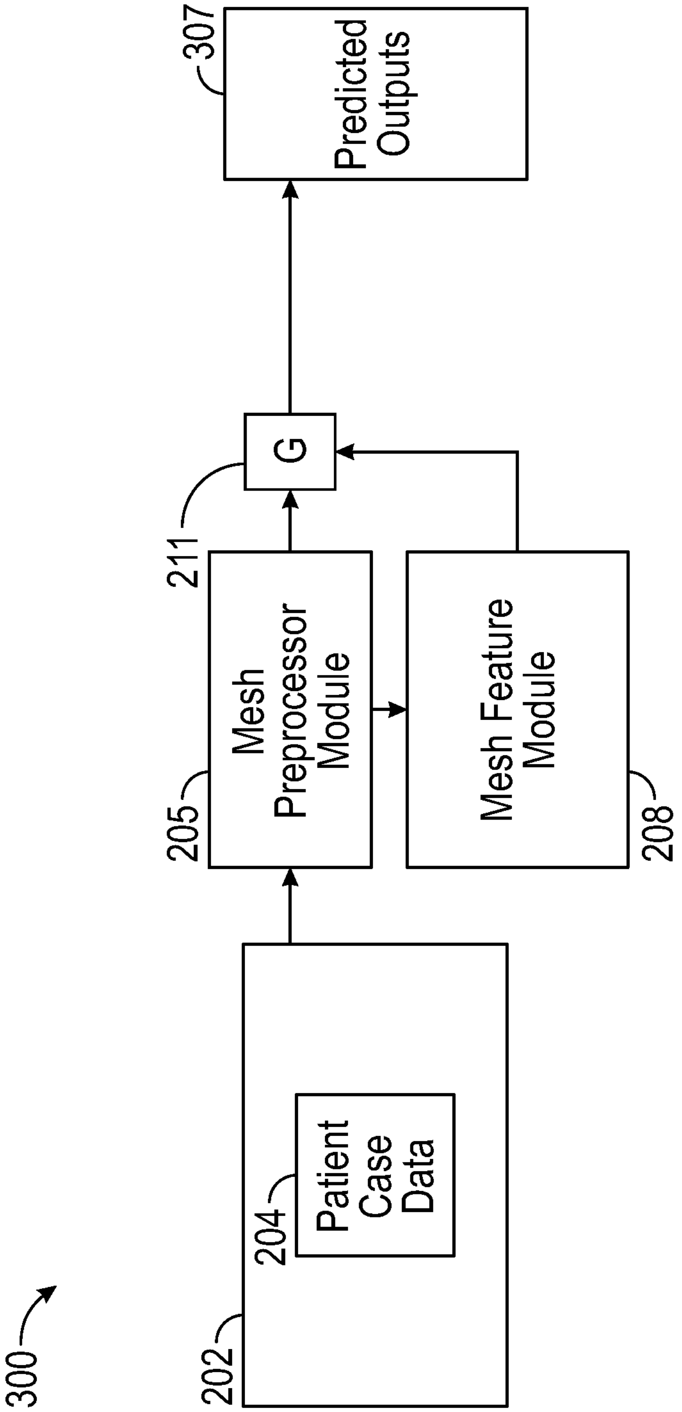
FIG. 3 shows an example generalized technique for using a trained generator or other neural network according to various aspects of this disclosure.

Once trained, generator 211 can be used to generate accurate predicted output 207 for patient case data 206 received by receiving module 202. One example technique 300 for generating predicted labels 207 is shown in FIG. 3. In general, technique 300 performs many of the same steps as technique 200, using the same computer modules and components. That said, as can be seen from the example, technique 300 does not train generator 211, and instead relies upon the training in technique 200 to generate the predicted outputs 307. Furthermore, technique 300 does not contain a discriminator. As should be appreciated from the discussion above with respect to FIG. 2, as the generator 211 is trained, predicted outputs 207 will eventually be equal or substantially equal to the predicted outputs 307.

Some of the techniques described in Table 2 (and elsewhere in this disclosure) may benefit from the training of representation learning models. Such a representation model may, in some implementations, be used to implement the generator 211 in FIGS. 2, 3, 4 and 5, module 811 in FIG. 8 and/or module 911 in FIG. 9. A representation learning model may, in some implementations, comprise a first module, which may be trained to generate a representation of the received 3D oral care representations (e.g., teeth, gums, hardware and/or appliance components), and a second module, which may be trained to receive those 3D representations and generate one or more output oral care representations. In some instances, such output oral care representations may comprise transforms which may be applied to hardware or appliance components, for placement in relation to one or more teeth. In some instances, such output oral care representations may comprise one or more coordinate system axis definitions. In some instances, such output oral care representations may comprise meshes or labels on mesh elements corresponding to teeth, gums or other aspects of dentition (e.g., such as with mesh cleanup, mesh segmentation or tooth restoration design).

In some implementations, the first module of the representation learning model may be trained to generate 3D representations for the one or more teeth (and/or gums or hardware) which are suitable to be provided to the second module, where the second module is trained to output one or more predicted transforms (or other oral care representations). In some implementations, one or more layers comprising Convolution kernels (e.g., with kernel size 5 or some other size) and pooling operations (e.g., average pooling, max pooling or some other pooling method) may be trained to create representations for one or more received oral care 3D representations in the first module. In some implementations, one or more U-Nets may be trained to generate representations for one or more received oral care 3D representations in the first module. In some implementations, one or more autoencoders may be trained to generate representations for one or more received oral care 3D representations (e.g., where the 3D encoder of the autoencoder is trained to convert one or more tooth 3D representations into one or more latent representations, such as latent vectors or latent capsules, where such a latent representation may be reconstructed via the autoencoder's 3D decoder into a facsimile of the input tooth mesh or meshes) in the first module. In some implementations, one or more 3D encoder structures may be trained to generate representations for the one or more received oral care 3D representations in the first module. In some implementations, one or more pyramid encoder-decoder structures may be trained to generate representations for one or more received oral care 3D representations in the first module. Other methods of encoding representations are also possible.

The representations of the one or more teeth may be inputted to the second module of the representation learning model, such as an encoder structure, a multilayer perceptron (MLP), a transformer (e.g., comprising at least one of a 3D encoder and a 3D decoder, which may be configured with self-attention mechanisms which may enable the network to focus training on key inputs), an autoencoder (e.g., variational autoencoder or capsule autoencoder), which has been trained to output one or more representations (e.g., transforms to place oral care meshes, such as those in the example of the hardware and appliance component placement techniques). In some implementations, a transform may comprise one or more 4×4 matrices, Euler angles or quaternions. The second module may be trained, at least in part, through the calculation of one or more loss values, such L1 loss, L2 loss, MSE loss, reconstruction loss or one or more of the other loss calculation methods found elsewhere in this disclosure. Such a loss function may quantify the difference between one or more generated representations and or more reference representations (e.g., ground truth transforms which are known to be of good function). In some implementations, either or both of modules one and two may receive one or more mesh element features related to one or more oral care meshes (e.g., a mesh element feature vector may be computed for one or more mesh elements for an inputted tooth, gums, hardware article or appliance component). The advantages of receiving the mesh element features are generally directed to improving the underlying system. For instance, such implementations allow the first module to more accurately represent the received 3D representations, and the second module to generate more accurate output 3D representation(s) (e.g., transforms, dental anatomy representations, or labels on mesh elements).

Figure 4:
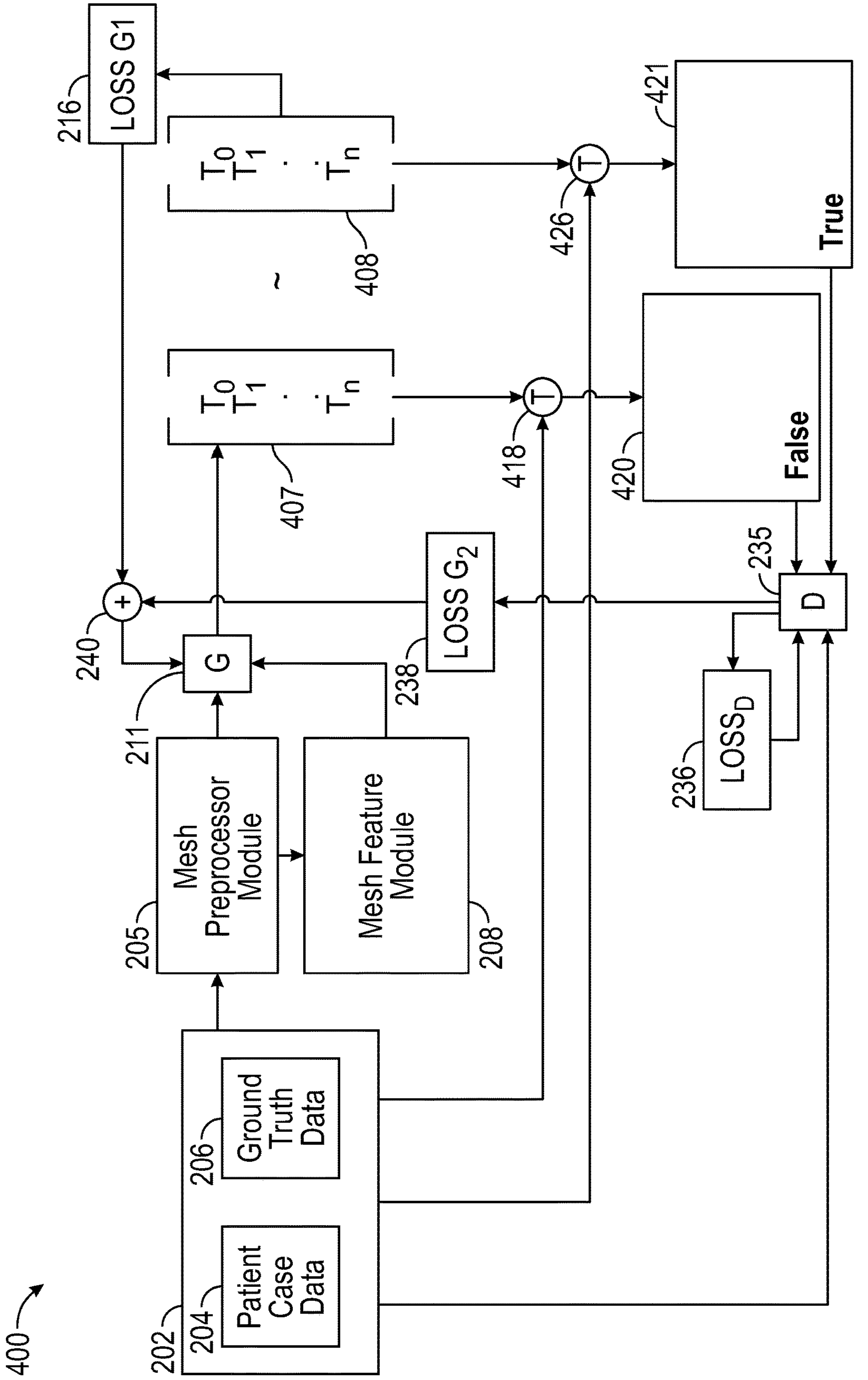
FIG. 4 shows another example generalized technique for training a generator or other neural network according to various aspects of this disclosure.
Figure 5:
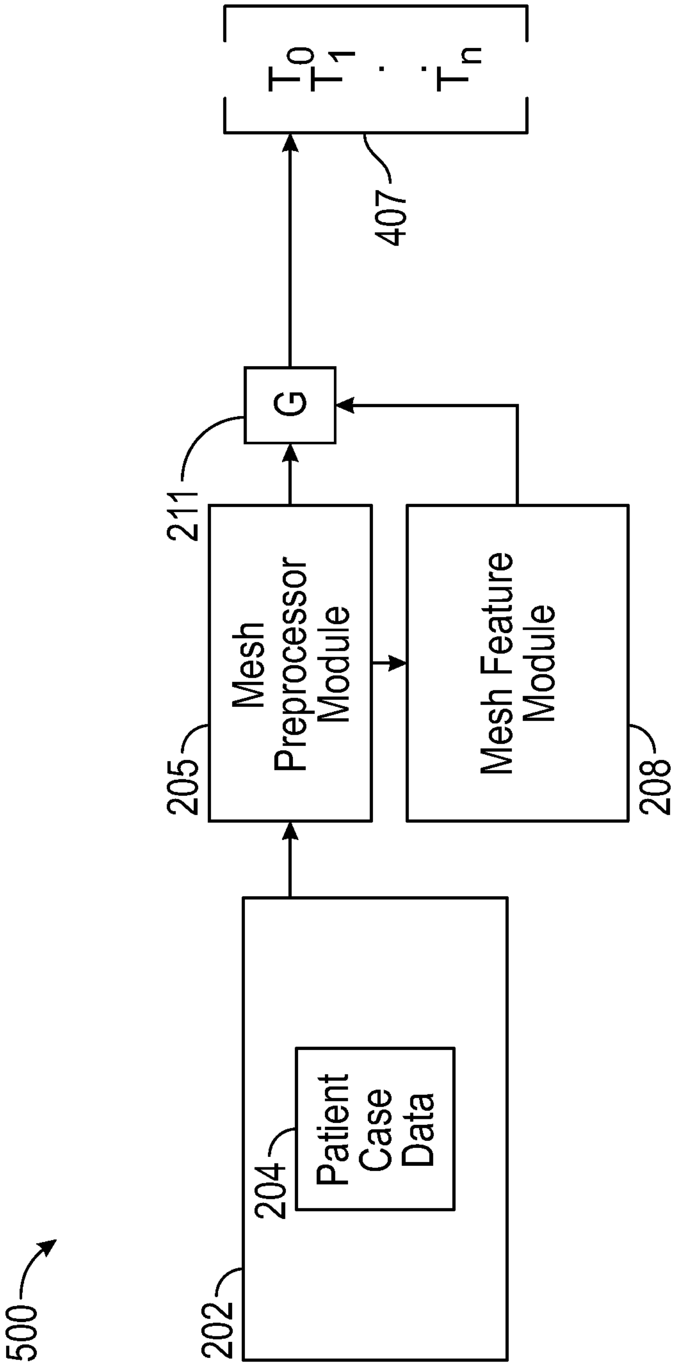
FIG. 5 shows another example generalized technique for using a trained generator or other neural network according to various aspects of this disclosure.

FIG. 4 depicts technique 400 for training an ML model, according to particular aspects of the disclosure. In general, technique 400 uses many of the same steps and concepts as those described in connection to FIG. 2, above. That said, certain additional aspects of FIG. 4 are now described. For instance, according to particular implementations, it may not be appropriate or correct to apply the predicted outputs directly to the patient data to generate the predicted representations. For instance, in segmentation based-implementations, applying one or more predicted labels to generate predicted representations 220, is appropriate because, e.g., the underlying representation of the patient data is not modified. Instead, in other implementations, the predicted outputs 407 can be one or more vectors that describe one or more transformations, and it may be necessary to apply an incremental processing step to apply those transformations to the patient data. For instance, when the predicted outputs 207 are predicted outputs vectors 407, a mesh transformer 418 can be used to apply the one or more predicted vectors to the patient data to generate the predicted representations 420. Similarly, when the reference inputs 207 are reference input vectors 407, a mesh transformer 426 can be used to apply the predicted vectors to the patient data to generate the predicted representations 421. Transformers 418 and 426 can use conventional techniques to apply the respective vectors to the patient data 204 to translate, scale, and rotate the patient data 204 to generate predicted representations 420 and reference representations 421, respectively.

One particular example pertains to coordinate system generation. Digital dentistry and digital orthodontics applications may require the definition of coordinate systems, to facilitate operations on 3D mesh models of teeth and gums. Some coordinate systems may be defined relative to an entire arch of teeth and are called global coordinate systems. Some coordinate systems may be defined relative to individual teeth and are called local coordinate systems.

In general, a tooth coordinate system comprises of a set of XYZ axes which are used to facilitate mathematical transformations and other operations on the tooth mesh. The tooth coordinate system functions relative to that tooth, with an origin located at a carefully chosen central location relative to the tooth mesh. The tooth's local coordinate system stands in contrast to the global coordinate system, whose origin is located in a location relative to the center of the whole dental arch. The global coordinate system is used to facilitate mathematical transformations and other operations on the dental arch as a whole. The correct choice of the tooth coordinate system is crucial to the proper functions of operations in the design of dental and orthodontic appliances relative to that tooth.

In implementations related to coordinate system prediction, each patient case in the dataset 204 consists of: 1) the set of segmented teeth in the arch; and 2) the set of transforms to describe the coordinate system relative to each of those teeth. In the depicted example, the generator 211 can be configured to generate one or more predicted vectors 407. Furthermore, the ground truth inputs 208 are represented in FIG. 4 as ground truth vectors 408. As already mentioned, both vectors 407 and 408 represent transformations to be performed on the patient case data 204 in order to generate one or more predicated representations 420 and ground truth representations 421, respectively. The vectors 407 and 408 can be of any size, but it has been observed that a vector having a dimension of 4×4 is well-suited to technique 400.

According to the depicted example, technique 400 uses mesh transformers 418 and 426, to transform the patient case data 204, generating predicted representations 420 and 421, respectively. Furthermore, and consistent with other aspects of the disclosure, for each predicted transformation (e.g., as defined by predicted vectors 407), the system 100 computes a LossG1 216 between that generated predicted vector 407 and the corresponding ground truth vector 408. LossG1 216 is fed back to update the weights of the generator 211. Additionally, as already described, both the generated vector 407 and the ground truth vector 408 are provided to the discriminator 235 (along relevant patient data 204, such as the tooth mesh). The discriminator 235 attempts to label vectors 407 and 408, distinguishing real (ground truth) from fake (generated).

According to particular implementations, generator 211 can be replaced with an encoder, which can be thought of as the first half of the U-Net structure depicted in FIG. 4. Specifically, an encoder can include any number of mesh convolution operators 402 and any number of mesh pooling operators 404, but does not typically include mesh un-pooling operators 406 or mesh un-convolution operators. That is, the mesh convolution operators 402 generate high-dimensional features for each mesh element by collecting that element's neighbor information based on the topology (i.e., based on mesh surface connectivity information). Mesh pooling operators 404 at each layer of the encoder simplifies the input mesh to a coarser resolution by reducing the count of mesh elements and summarizing the neighbor features for each element. The summarized high dimensional features at the last layer are further processed by multiple fully connected layers and eventually transformed into the final regression output (e.g., a transformation matrix that corresponds to a tooth coordinate system for a tooth movement in 3D).

The techniques disclosed herein may, in some implementations, predict two orthogonal coordinate axes concurrently.

From these two orthogonal coordinate axes, a third coordinate axis may be computed, for example using the Gram-Schmidt process.

According to particular implementations, the coordinate system predictions operate on a six-dimensional representation. Furthermore, while it is possible for coordinate system predictions to be made using technique 400 on a point cloud (e.g., a 3D point cloud), it is advantageous to perform coordinate system predictions on 3D geometry, such as 3D meshes. That is because, in general, a 3D mesh (as opposed to a 3D point cloud) is more accurate in the ability to capture the local surface structure of the object. For example, two surfaces could be very close in Euclidean Space, and yet be very far apart from each other in a mesh topology (or in geodesic space). Therefore, a 3D mesh is a better choice for representing surfaces.

Furthermore, for edges vs. vertices, a vertex element in the 3D mesh could have infinite (in theory) connected neighbor vertices, while an edge element in the 3D mesh has a fixed number of neighbor edges (e.g., 4 neighbors). A boundary edge can be given two dummy edges to make the number four. The use of a mesh makes mesh convolution in 3D more straightforward. The fixed number of neighbors also makes the mesh convolution output relatively more stable during training. From the mesh topology perspective, the number of edges in a 3D mesh is typically greater than the number of vertices (e.g., typically by a factor of 3×). In a sense, mesh resolution can be increased by using edges for predictions, because there are so many more edges than vertices in atypical mesh. Furthermore, it should be appreciated that neural networks, generally, benefit from training on a larger number of elements. Thus, by using 3D meshes, the resulting inferences are improved, and the benefit is passed along to later post-processing steps yielding an overall more accurate system.

Similar to the relationship between FIGS. 2 and 3, once trained, generator 211 can be used to generate accurate predicted vectors 407 for patient data 204 received by receiving module 202. One example technique for generating predicted vectors 407 is technique 500 shown in FIG. 5, which shares many of the same characteristics as techniques 300 and/or 400, described above.

Figure 6:
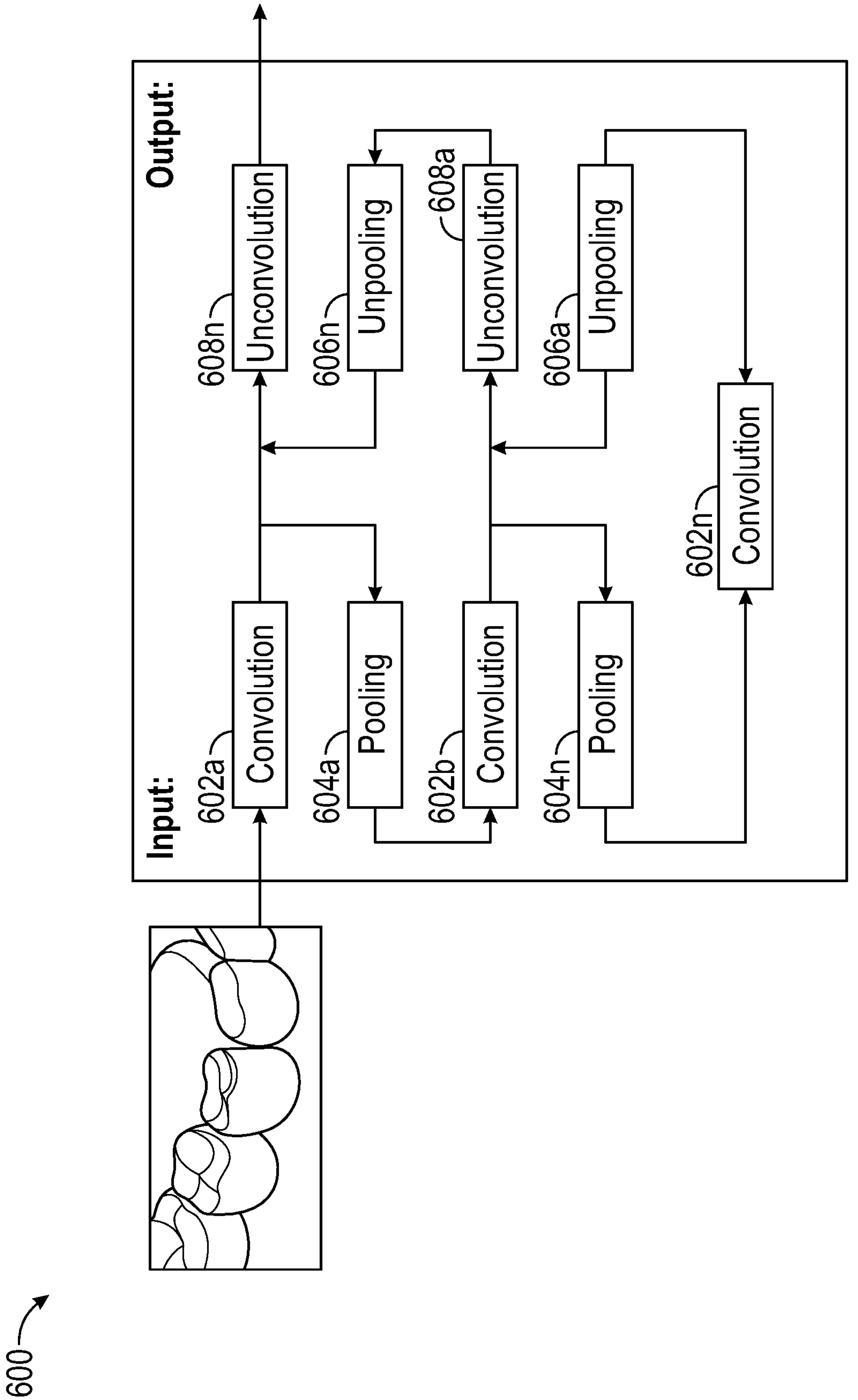
FIG. 6 shows an example machine learning architecture, in accordance with various aspects of this disclosure.

FIG. 6 is an illustration of an example ML architecture 600 that can be used by system 100 for designing and manufacturing a dental appliance for restoring the dental anatomy of a patient, in accordance with various aspects of this disclosure. For instance, many of the techniques described herein rely on some form of architecture 600 as the basis for the ML models described herein.

In the depicted example, the ML model 600 is a U-Net architecture. The eponymous architecture is configured as one or more mesh convolution operators 602*a*-602*n*, mesh pooling operators 604*a*-604*n*, mesh unpooling operators 406*a*-406*n*, and mesh unconvolution operators arranged in an inverted pyramid, or "U" shaped configuration. Used herein, it should be appreciated that the term "operator" is synonymous and used interchangeably with the terms "node" and "layer," which are also used to describe similar operations in ML parlance.

In general, the U-Net architecture 600 involves mesh pooling and mesh unpooling operations, which aid the process of extracting mesh element neighbor information. Each successive pooling layer helps the model learn neighbor geometry info by decreasing the resolution, relative to the prior layer. Each successive mesh unpooling layer helps the model expand this summarized neighbor info back to a higher resolution. A sequence of mesh pooling layers followed by a sequence of mesh unpooling layers will enable the efficient and accurate training of the U-Net and enable the U-Net to output features for each element that contain both local and global geometry info.

According to particular implementations, one purpose of the U-Net architecture 600 is to compute a high-dimensional feature vector for the input mesh. For instance, according to particular implementations, the U-Net architecture 600 computes a feature vector for each mesh element (e.g., a 128-element feature vector for each edge, vertex, or face element). This vector exists in a high dimensional space which is capable to represent the local geometry of the edge within the context of the local tooth, and also represent the global geometry of the two arches. The high dimensional features for the elements within each tooth are used by the encoder to make predictions. The accuracy of the prediction is aided by the combination of this local and global information. The combination of local and global information enables the U-Net architecture 600 to account for geometrical constraints. For example, during the course of a clear tray aligner treatment, it is undesirable for teeth to collide in 3D space. The combination of local and global information enables the U-Net architecture 600 to generate transforms which reduce or eliminate the incidence of collisions, and therefore yield greater accuracy relative to prior techniques. Upon the occasion that a collision does occur, the techniques of WO2020/136587A1 "Methods to automatically remove collisions between digital mesh objects and smoothly move mesh objects between spatial arrangements" can be used to detect and remove that collision between the tooth meshes of the arch. In keeping with that disclosure, geometrical quantities such as penetration depth, penetration direction, and count of overlapping mesh elements (such as vertices) may be computed, in keeping with the detection and removal of tooth mesh collisions. Mesh shapes and/or positions may be perturbed or changed, in keeping with the content of that disclosure, to reduce or eliminate the incidence of collisions which may in some instances remain after the operations of the neural networks structures of the present disclosure. In general, information provided to the ML model 600 is first processed by being propagated "downward" through operators 602*a*, 604*a*, 602*b*, 604*n*, etc., until the information reaches the bottom operator (here represented by mesh convolutional operator 602*c*). Then, the information is propagated "upward" through operators 606*a*, 602*d*, 606*n*, etc., until the information is outputted by the final mesh convolutional operator 402*n*, which can be used by various aspects of the present disclosure, as will be described in more detail below.

The example U-Net architecture shown in FIG. 6 is depicted with a total of nine layers (or nine operators), but it should be understood and appreciated that the U-Net architecture can be configured with any number of convolutional layers, any number of mesh pooling layers, and any number of mesh unpooling layers to achieve the desired results.

In general, each of operators 602*a*-602*n*, 604*a*-604*n*, and 606*a*-606*n* can be configured using conventional techniques to modify received inputs pertaining to 3D mesh data (including, e.g., mesh size and pose, as embodied by edge lengths, edge curvatures, edge normals, edge midpoints and other edge data) to produce specific output that is appropriate for each of the operators 602*a*-602*n*, 604*a*-604*n*, and 606*a*-606*n*, as will be described in more detail below.

According to particular implementations, the mesh convolution operators 602*a*-602*n* that are disclosed in the instant disclosure can be configured to be agnostic to the size and pose (e.g., position and/or orientation) of the input 3D mesh, according to particular implementations. The advantage of this agnostic approach is that mesh cleanup operators can be used to handle arbitrarily oriented raw input meshes, as opposed to input meshes of a fixed size and/or orientation.

In other implementations, however, size and pose information is desired, such as in the context of regression operations. In implementations where size and pose information is desired, the convolution operation can instead be configured to not be agnostic to size and pose information. For instance, convolutional filters used as part of the convolution operators 602*a*-602*n* ML model can be specifically configured to be sensitive to size and pose information when such systems should not be agnostic to that information. In other implementations, there may be specific aspects of an operation that are benefited from size and pose information. One specific example is for 3D mesh segmentation, which is benefited from the size and pose agnostic mode under some applications (e.g., the segmentation of gingiva—which is used to find the general region of the intraoral scan that contains the teeth), but not under other applications (e.g., tooth segmentation—which benefits from information about left and right sides of a mesh). As a result, it should be appreciated that within specific types of tasks (e.g., segmentation tasks), the aspects of the ML model can be configured to be size and pose agnostic for those operations that are benefited, and other aspects of the ML model can be configured to be size and pose sensitive for those operations.

Mesh pooling operators 604*a*-604*n* are configured to resample the input mesh into a lower resolution. As a result, through each successive layer of mesh pooling operators 604*a*-604*n*, the mesh is continually refined and resampled into a lower resolution. This allows for downsampling, or shrinking, of the mesh input. For instance, a downsampling of information in 3D space may take a 3×3×3 set of information and combine it into a single 1×1×1 representation. In the context of 3D mesh information, for example, four neighbor edges of a given edge will be combined into a single edge at the next resolution level. The mesh resolution (mesh surface area) after downsampling will be decreased by a factor of 4×.

One of the many advantages of this approach is that the Mesh pooling operators 604*a*-604*n* result in each feature collecting that neighbor's information and summarizing the information into a form that is passed to the next layer. Consequently, as the mesh information moves through the U-Net architecture 600, the output of the lowest-level convolution operation 602 (such as 602*c* in the depicted example) takes the form of a down-sampled mesh that reveals global information about the original input mesh. Stated differently, the output of the lowest-level convolution operation 602 is considered to constitute fully summarized information and that can be used in accordance with various techniques of this disclosure. For instance, the down-sampled output of the lowest-level mesh convolution operation 602 can be used in classification operations (e.g., for 3D validation), and regression operations (e.g., for coordinate system prediction), to name a few examples.

In addition, the fully summarized information can undergo further processing by additional operators (e.g., depicted as operators 602*n*, 604*n* and 606*n*). For instance, the fully summarized information output by operator 402*c* can be processed by the mesh unpooling operators 606*a* and 606*n* to increase the resolution of the mesh information. As depicted in the example ML model 600, there is a 1:1 relationship between mesh pooling operators 604*a* and 604*b* and mesh unpooling operators 606*a* and 606*n*. That is, after a sufficient number of mesh unpooling operations (performed, e.g., by operators 606*a*-606*n*) equivalent to the number of mesh pooling operations (performed, e.g., by operators 604*a*-604*b*) have been performed, enough information is surfaced that allows other automated techniques to identify classes of elements (e.g., edges, faces, vertices) in the 3D mesh. This, for example, allows the automated system to perform mesh segmentation (e.g., performing tooth segmentation, gingiva segmentation, facial-lingual segmentation, etc.) on the output of convolutional operator 602*n*.

Figure 7:
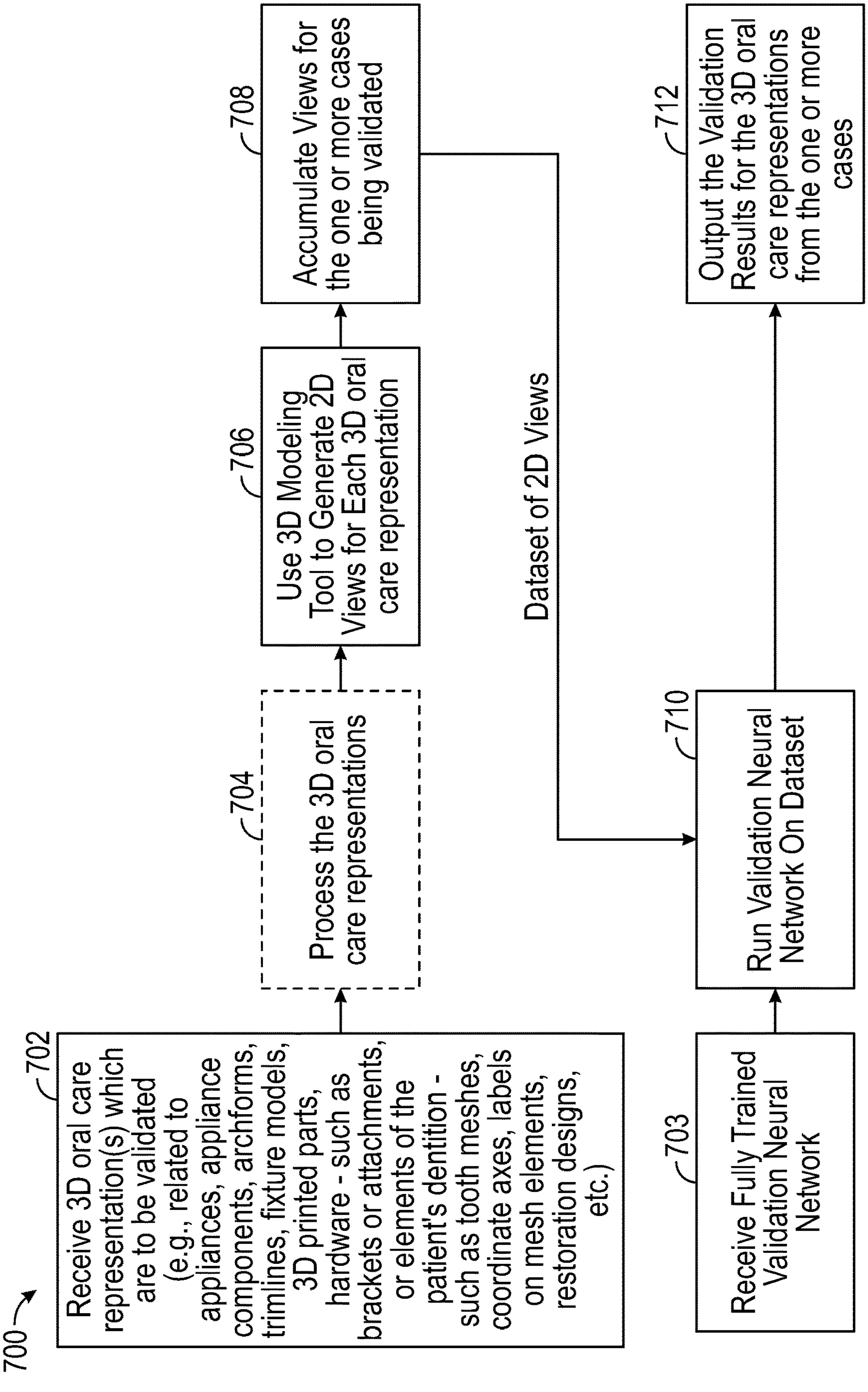
FIG. 7 shows an example technique for performing 2D validation on dental data.

FIG. 7 is an example technique 700 of automatically validating neural networks trained using techniques described herein.

In general, an ML model can be trained to validate datasets to be used for digital dentistry or digital orthodontics. In some implementations, an ML model, such as a neural network can be used to validate 2D raster image views of the 3D data. One example neural network is a convolutional neural network (CNN). Numerous views can be produced of the 3D data. The CNN is used to classify each view (e.g., as correct or incorrect), and the validation results of the plurality of those 2D raster views can be used to validate the correctness of the 3D data. In other implementations, the neural network can be a general-purpose deep neural network for 3D triangular meshes, such as a MeshCNN. MeshCNN is an open-source neural network implementation. MeshCNN uses the geometric deep learning (or GDL) technique which involves a first method of performing mesh processing which operates on edges (or other mesh elements, such as vertices or faces) to implement mesh convolution, mesh pooling, mesh unpooling, mesh unconvolution and other 3D-specific Deep Learning techniques. The open source Minkowski Engine includes a GDL-capable neural network which additionally provides for the GDL operation of sparse convolution. Sparse convolution is a convolution technique which has different representational data from that of the mesh convolution operation found in MeshCNN (i.e., voxels). Voxels are used in the sparse convolution operation. Voxels are the 3D geometry equivalent of pixels in 2D images. Sparse convolution techniques take advantage of the sparsity of data to make 3D volume processing more efficient in many cases. This improvement in efficiency is important because some problems may be intractable otherwise. In other words, GDL techniques may be applied to each of the GDL examples of this disclosure, including all of the 3D validation techniques, mesh segmentation, mesh cleanup, mesh coordinate system prediction, restoration prediction, restoration appliance component placement and generation, as well as bracket and attachment placement.

In these implementations, the MeshCNN can be used to directly validate the correctness of 3D data without having to rely on 2D raster image views of the 3D data. In some implementations, the results of one of those validation operations can be fed back into an automated process, to improve a further iteration of the process that generated those 3D data. In other implementations, the results of one of those validation operations can be reported or displayed to a human technician who can then proceed to correct issues with those 3D data. In other implementations, 2D data, such as photographs of dental or orthodontic appliances, can be directly validated using an ML model, such as a neural network. In some implementations, the data to be validated may describe a patient's dental geometry, possibly including teeth and/or gums. In other implementations, the data to be validated may describe a dental or orthodontic appliance, or a component thereof. In some implementations, the validation inventions described in this disclosure may be integrated into automated testing suites (e.g. unit testing and regression testing for software and algorithms). In other words, while a neural network is a preferred ML approach, other ML techniques can be used as appropriate.

For instance, a MeshCNN can be trained on two (or more) classes of data, for example, 3D meshes corresponding to the RAW class (the "raw" output from segmentation) and 3D meshes from the TECH class (the meshes that were modified or corrected by a technician). The MeshCNN would become able to distinguish between the two classes and could be used in a setting where teeth must be segmented for use in dental or orthodontic appliances, among other applications. In some instances, the RAW class may correspond to a suboptimal state, and the TECH class may correspond to an optimal state. In the 3D case, either a MeshCNN or an encoder can be trained to distinguish between these classes. In the 2D case, a CNN can be trained to distinguish between these classes. This approach can apply to the other validation operations of this disclosure, as well. Operational validation engines used in deployment are designed to detect flaws in 3D geometry (e.g., dental or orthodontic geometry). Such an operational validation system may be trained on RAW and TECH classes of data as a stand-in for the categories of CORRECT and INCORRECT which the validation engine may encounter in the field, through the course of operational use. This pertains to each of the validation applications described in this disclosure (e.g., segmentation validation, mesh cleanup validation, coordinate system validation, dental restoration appliance component validation, 3D printed part validation, trimline validation, fixture model validation and restoration design validation).

Turning now to the example depicted in FIG. 7, in step 702, a system, such as system 100 receives one or more 3D oral care representations, such as 3D meshes of a patient's dentition (which may include information pertaining to the patient's teeth, gingival tissue, and other aspects of the patient's oral anatomy) as well as other information. The received 3D meshes can differ depending on the particular purpose. For instance, in implementations concerning mesh segmentation, the received 3D information may pertain to an arch of the patient's mouth, which may include 3D representations of teeth and/or gingival tissue, implementations for validation of hardware or appliance component placement. The received 3D meshes may include 3D representations concerning specific teeth and associated hardware. In implementations concerning the validation of 3D printed parts, the received 3D meshes may include 3D mesh data related to the part being examined in the form of a CT scan, or other diagnostic imagery, to name a few additional examples.

In step 703, the system 100 can receive a fully trained neural network, such as a fully trained generator 211 described above.

In step 704, the system 100 may optionally process the received 3D oral care representations in preparation for subsequent steps. For instance, in one implementation, the system 100 can generate or otherwise place components for a dental restoration appliance on corresponding teeth in the 3D mesh that must be validated. In another implementation, the system 100 could place brackets or attachments (or other hardware, like buttons or hooks that attach to the teeth, to which resistance bands may be attached to the buttons or hooks) relative to particular teeth among the 3D oral care representations. In a related implementation, the system 100 could predict a coordinate system for one or more teeth (e.g., comprising one or more local coordinate axes per tooth). In yet other implementations, the 3D oral care representations can be processed to promote the identification or labelling of the mesh elements in a 3D mesh (or 3D point cloud) of a patient's dentition. Examples where this may be useful include the applications of segmentation (e.g., tooth segmentation), of mesh cleanup or of automated restoration design generation. In another implementation and with respect to segmentation, a particular tooth may be labeled as being either correctly segmented or incorrectly segmented. Other types of validation regarding other aspects of the present disclosure are also possible. Stated differently, there are potentially many ways to train a neural network which can validate 3D oral care representations, according to the specifics of the particular implementation.

In step 706, the system 100 may use a 3D modeling tool to generate a number of 2D raster views for each tooth. According to particular implementations, a 3D modeling tool such as GEOMAGIC can be used, for example by way of an automated script. Other 3D modeling and rendering engines may be used, in some examples. Used herein, a view can be defined as a specific orientation of the camera inside the modeling tool that provides a specific representation of the 3D mesh with the 3-dimensional space represented in the modeling tool. In other words, at step 706, the camera within the modeling tool can be positioned such that each tooth in the 3D mesh is viewed from a slightly different angle or vantage point within the modeling tool. The number of views that are generated can vary according to particular implementations, or the particular use case. For instance, according to one implementation, fifteen different views of the 3D meshes are generated, although any number of views can be generated for a specific tooth. Consequently, if fifteen views are generated at step 706, for a patient having thirty-two teeth, a total of 480 2D images can be generated for the patient's mouth, at step 806 to name one example.

According to particular implementations, the 2D raster images generated in step 806 can be used as a comparator when performing other techniques described herein. For instance, with respect to tooth segmentation, a segmented tooth mesh (e.g., generated in step 804) can be overlaid on top of the 3D mesh data received in step 802. Then, aspects of the 2D raster images that align with scan data can be identified. For instance, in one implementation, the result of the overlay is a red-colored portion of the geometry which corresponds to the segmented tooth mesh and a blue-colored portion of the geometry corresponds to the scan data.

One advantage of applying a visualization treatment, such as the one described above, is that such a visualization allows human users to identify potential misclassification of the training data. Additionally, applying what is essentially a binary treatment to the teeth allows for the training of the two-classification ML model (as described elsewhere in the specification) to provide accurate predictions. It should be appreciated that, without the loss of generality, each of the 2D and 3D validation examples of the instant disclosure may operate under n-class classification, for example in the case that there are multiple 'correct' validation outcomes and multiple 'incorrect' validation outcomes.

In step 708, the system 100 can accumulate or otherwise aggregate 2D views over a number of patient cases. For instance, according to one implementation, sixty patient cases can be used. In other words, if there are 480 2D images generated for each patient, then in implementations using sixty patient cases, the training data can include 28,800 different 2D images, to name one example.

In step 710, the system 100 can train the neural network received in step 703 to validate the accumulated views of the one or more cases. For instance, as it relates to validating digitally generated setups for orthodontic alignment treatment, running the fully trained neural network can specify one or more criteria scores that specify whether one or more aspects of the received views of the generated setups is correctly formed.

In step 712, the system 100 outputs both the test results and the resulting neural network. For example, according to particular implementations, the outputs can specify whether the received 3D meshes pass the validation check. If the received 3D meshes do not pass the validation check, the output may also include corrections to the received information describing one or more corrective measures. For instance, if the 3D meshes represented scans of 3D printed parts, the corrective measures may describe how to modify the already fabricated 3D printed parts to fit the patient's dental anatomy. Various conditions can be measured or otherwise analyzed in this way. For instance, the technique can measure whether the generated setups are correctly formed measure criteria concerning the alignment, marginal ridges, buccolingual inclination, occlusal relationships, occlusal contacts, overject (or overbite), interproximal contacts, and root angulation to name a few examples. In other examples, the corrective measures may provide guidance on how to correct the functioning of the 3D printer (e.g., to resolve a partially clogged nozzle which led to a malformed 3D printed part).

While technique 700 is described using neural networks, it is also possible to perform one or more steps of technique 700 using ML models other than neural networks, such as support vector machines (SVN), random forest, K-Nearest Neighbors (KNN), and other ML models. To appreciate how such other ML models may be used, the data can be split into two classes of data "TECH" (class 01) and "RAW" (class 00) data. The TECH class is the data which result from manual intervention by the expert technician. The RAW class is the data which are output from an automation tool. The TECH class data may generally represent a more correct dataset than the RAW class data, since the TECH class data have been fixed/improved/tweaked by an expert technician. The following methods pertain to non-neural network approaches to distinguishing between the TECH (class 01) and RAW (class 00) classes.

For an effective texture feature-based validation classifier, combining segmentation marks via color with the tooth/gum geometries may yield different kinds of artifacts for each class. There are a number of existing texture feature descriptors that can be used as part of a texture feature-based validation, including HOG, SURF, SIFT, GLOH, FREAK, and Kadir-Brady. These texture-based validation classifiers can be used by less complex ML models, like some image augmentations may improve the classifier, such as increasing the contrast between tooth and gum segmentations such that feature vectors find more differences around the tooth/gum line when comparing computer and technician generated segmentations. Each of the validation applications of this disclosure may describe implementations which involve texture feature-based operations.

For instance, using texture feature-based validation utilizing SIFT classification may include the optional step of converting training images to grayscale, and the steps of finding SIFT keypoints on each image, generating descriptors of those keypoints, selecting only the top N descriptors (where N is the fewest number of descriptors found in all training sample input images) and training an support vector machine (SVM) model on the image descriptors. Other implementations may replace training the SVM model on the image descriptors, e.g., with fitting a k-nearest neighbors (KNN) classifier on the image descriptors, to name one example.

That said, while the more simplified non-neural network ML models can be used, there are various advantages to using a neural network approach. For example, a neural network can be designed with a sufficiently large number of parameters (i.e., weights) to encode solutions to complex problems, such as understanding 2D raster image views and 3D geometries (i.e., 3D meshes). Furthermore, texture features may not detect all of the relevant attributes of the image, for example, attributes which are indicative of defects or errors which the validation process means to detect.

Figure 8:
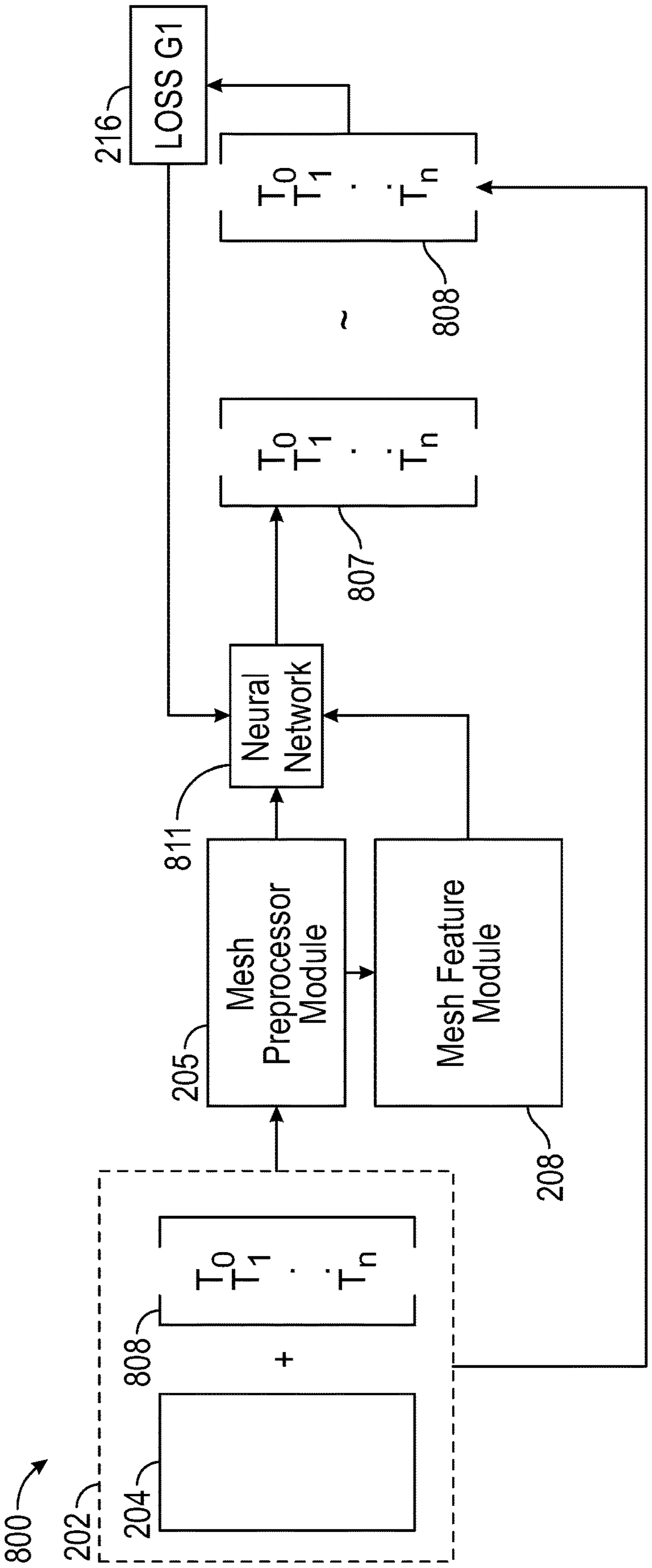
FIG. 8 shows an example technique for training an encoder.

FIG. 8 shows an example technique 800 of validating the output of ML models, in accordance with various aspects of this disclosure. In general, and used herein, to "validate" an output of an ML model means to inspect that output for quality and correctness, e.g., automatically by an ML technique, such as a neural network. The term "validation" is used in an additional context, to refer to a small dataset (perhaps 10% of the total data), which is used to assess the progress of an ML model (such as a neural net) as training proceeds. That said, unless specifically referred to as validation data, as used herein, validating output is generally intended to mean checking the correctness of output produced by an ML model.

In general, the approach in the depicted example involves an encoder structure (e.g., represented by encoder 811). That is, according to particular implementations, the generator 211 can be encoder 811 that can be trained to classify 3D meshes into different categories (i.e., good/bad, or correctly-formed/not-correctly formed). The encoder 811 described herein is further configured to output one or more vectors of probabilities (e.g., vector 812). Each element in the vector 812 corresponds to a class or category of label to be applied to the input mesh. The vector element with the highest probability value signifies the determination or output of the encoder 811. This encoding scheme is called one-hot encoding. During the training of the encoder, each of the training samples (i.e., 3D meshes) has an associated "ground truth" label in the form of a one-hot vector (e.g., vector 814). This vector may contain a 1 in the element that corresponds to the intended mesh category, and a 0 in each of the other elements.

As in FIG. 8, technique 800 utilizes the receiving module 202 which receives patient case data. According to particular implementations, the receiving module 202 can receive patient data 204 corresponding to 3D meshes pertaining to one or more aspects of one or more patient's dentitions. That is, patient data 204 can differ based on the dental and/or orthodontic treatments to be performed on the patient. According to particular implementations, the patient data 204 can include one or more dental arches and malocclusion arch geometries, or other mesh data not depicted in FIG. 8. For instance, in implementations concerning validation of bracket placement, the patient data 204 may only include 3D mesh data concerning specific teeth and associated brackets, whereas in implementations concerning the validation of 3D printed parts, the patient data 204 may include 3D mesh data related to the part being examined in the form of a CT scan, or other diagnostic imagery, to name a few additional examples.

The receiving module 202 also receives ground truth data 208 in the form of one or more vectors 908 that corresponds to "ground truth" one-hot vectors. In general, these "ground truth" vectors 908 specify an expected result of applying other techniques disclosed herein, be it mesh segmentation, coordinate system prediction, mesh cleanup, restoration design, and bracket/attachment placement, and all of the validation applications of the disclosure, to name a few examples. According to particular implementations, the "ground truth" vectors 808 can be predefined or provided as a result of the outcome of performing one or more other techniques disclosed herein.

The resulting information generated by mesh feature module 208 and the patient data 204 can be provided to encoder 811. Again, as described above, the encoder structure 811 is configured to generate one or more predictions, represented by prediction vector(s) 807.

Once the one or more prediction vectors 807 are generated, they are compared against the "ground truth" vectors 808. During the neural network training process, a loss value (e.g., loss value G1 216) is computed for each of the training samples. This loss is produced through a cross entropy computation on two one-hot vectors: the "ground truth" vector associated with an individual training mesh, and the "prediction" vector that is produced by the encoder 811 in response to that training mesh. This loss value is fed back into the encoder 811 to further refine the encoder 811, for example using backpropagation techniques.

Other training techniques are possible, as are other loss functions. For instance, as described above in reference to FIG. 2, the neural network can be trained using one or more generated inference metrics which can be provided to the neural network after an execution of the neural network generates one or more prediction vectors 807 to further refine the weights of the neural network.

In some implementations, the mesh samples used for training the neural network may be duplicated and those duplicated meshes may be augmented to increase the supply of training samples and assist the neural network in training. The training process is aided by exposing the neural network to a wider array of possible inputs. 3D mesh processing operations which may be involved in the production of this augmented dataset include but are not limited to: normalization, rotation, translation and non-uniform scaling. In some implementations, these operations may be applied to the vertices of a mesh, to change the mesh and increase the scope of possible meshes that the neural network sees over the course of training. In other implementations, augmentation steps may be applied to edges or faces of the mesh.

The validation technique 800 can be used in various aspects of the present disclosure. For instance, table 3 illustrates the types of validation that can be performed using technique 800 and the patient data 204 received to perform the respective validation.

TABLE 3

| Validation Technique | Patient Data 204 |
|---|---|
| Tooth segmentation validation | Full arch of clean-up teeth, including gingiva |
| Facial-lingual segmentation validation | Full arch of clean-up teeth, including gingiva |
| Validation of mesh cleanup | Full arch of clean-up teeth, including gingiva |
| Validation of mesh cleanup via gingival segmentation | Full arch of clean-up teeth, including gingiva |
| Validation of mesh cleanup via trimline segmentation | Full arch of clean-up teeth, including gingiva |
| Coordinate system validation | Tooth and associated coordinate axes (e.g., X-Y-Z axes) |
| Validation of final setups and intermediate stages | One or more tooth meshes in a spatial arrangement |
| Validation of dental restoration appliances and appliance components (either or both of placed and generated components) | One or more generated components, one or more library components, and/or one or more teeth |
| Validation of bracket or other hardware placement | Tooth and associated bracket(s) or (other hardware) |
| Validation of attachment placement | Tooth and associate attachment(s) |
| Validation of 3D printed parts | 3D mesh of the fabricated part to be examined (e.g., by way of a CT scan) |
| Validation of dental fixture models (e.g., those used for thermoforming aligners or indirect bonding trays) | 3D mesh of the fixture model, which may include teeth, gums, hardware and/or a base |
| Validation of a clear tray aligner (CTA) trimline, which defines the cutting path to cut a clear tray aligner off of a fixture model | 3D mesh or polyline representing the CTA trimline, and a 3D mesh of the teeth (possibly as a part of a fixture model) |
| Validation of an archform | At least one of: a set of n control points through which a spline may be drawn (e.g., a B-spline), a 3D polyline, a 3D mesh, or a 3D surface. May be validated in conjunction with teeth, gums and/or other elements of dentition. |

For instance, with respect to segmentation, system 100 can be configured to receive a first digital representation of a patient's dentition, which has been assigned labels by a neural network consistent with other aspects of this disclosure. The system 100 can also receive a second digital representation of the patient's teeth, which has predefined labels assigned thereto. Then, the system 100 can determine whether the labels on the one or more aspects of the first representation are substantially similar to the labels on the corresponding one or more aspects of the second representation, generate an output that describes whether the labels are substantially similar (e.g., in the form of a loss value), and the use that process to further train the neural network that provided the classification (e.g., using that loss value to train the neural network via backpropagation). Mesh cleanup also deals with labeling mesh elements. Whereas segmentation applies labels to mesh elements and mesh elements with like labels are copied into new meshes (e.g., each tooth is copied into its own mesh—process known as tooth cutting), mesh cleanup applies other operations to the labelled mesh elements. Mesh cleanup may remove all mesh elements with a certain label or labels from the mesh. In other implementations, mesh cleanup may perform metrics calculations on all mesh elements with a certain label or labels. In still other implementations, mesh cleanup may apply transformation operators such as translation or non-uniform scaling on all mesh elements with a certain label or labels.

Similar approaches can be used for other applications. For instance, with respect to segmentation validation, the system 100 can be configured to receive one or more arches, where the arches are 3D meshes, each mesh is comprised of elements (such as vertices, edges and faces), and each mesh element has been assigned a predicted label. A ground truth label for each mesh element is also supplied to the system 100. A validation neural network can be trained to compare the predicted labels to the ground truth labels. According to one implementation, this comparison can be performed on 3D mesh data using a neural network such as a MeshCNN to classify meshes. In other implementations, this comparison can be performed on 3D mesh data using an encoder structure to classify meshes. In other implementations, this comparison can be performed using a neural network, such as a CNN, to classify 2D raster image views of teeth and gums, where the neural network is trained on a first set of images of teeth and gums which have been colored according to the predicted labels on the mesh elements, and a second set of images of teeth and gums which have been colored according to the ground truth mesh elements. These examples can also be extended to mesh cleanup validation, which also involves the training of neural networks (either 2D or 3D) to compare a set of predicted mesh element labels to a set of ground truth mesh element labels. Similar 2D and 3D validation examples also apply to applications such as CTA trimline validation, fixture model validation, the validation of 3D printed objects, the validation of dental restoration designs and the validation of bracket and attachment placements.

In another example, with respect to coordinate system validation, the system 100 can be configured to receive one or more first coordinate axes, one or more second coordinate axes, and a representation of the patient's dentition (including, but not necessarily limited to a representation of the patient's teeth) to determine whether the first and second coordinate axes are substantially similar. According to one implementation, this comparison can be performed by generating a representation of the teeth in proximity to a representation of both the first and second coordinate axes. The presentations can be 2D images, 3D data and other presentations, including combinations thereof.

As another example, validation can be used on the placement of a library component for a dental restoration appliance or other oral care appliance. The library component comes from a fixed set of static designs. This validation neural network inspects the position and orientation of the library component relative to the teeth. The input consists of the library component and one or more teeth. Whereas the generated component can be inspected either in isolation or with respect to one or more teeth, the library component must be inspected with respect to one or more teeth.

In some implementations the one-hot vector of output predictions contains two elements, one containing the probability that the input mesh(es) received the predicted validation outcome of 'correct', and the other containing the probability that the input mesh(es) received the predicted validation outcome of 'incorrect'. In the 'correct' case, the library component is deemed to be properly located and oriented relative to the relevant teeth, and therefore suited to the construction of a dental restoration appliance. In the 'incorrect' case, the library component placement needs further work, either by a technician or by a further iteration of an automated process. Similar validation outcomes apply to the other validation aspects of this disclosure, according to the particulars of those implementations.

It should also be appreciated that each of the validation operations described in this disclosure (and shown in Table 3) shares the possibility of a feedback loop, whereby when the validation outcome yields a failing result, the notification can be set to the process which created that geometry (e.g., an automated process) to tell the process that the geometry should be re-created. In this way, several iterations of geometry validation and geometry regeneration can be executed, to improve the suitability of that geometry for use in creating a dental or orthodontic appliance. In some implementations, an indication can be outputted by the validation process which indicates how to improve the next iteration of geometry creation/re-generation.

Techniques described in this disclosure can also be modified to implement regression testing on the outputs of the various techniques to verify that any changes to the various techniques, either by way of changes to the neural network or other changes to not adversely affect the accuracy of outputs generated by those techniques. For instance, techniques such as mesh segmentation, mesh cleanup, coordinate system prediction, restoration design generation, bracket/attachment placement all output geometry which can be validated by regression tests or unit test. Such a test may be run to ensure that recent source code changes to any of the source code modules needed to perform a particular technique have not broken or rendered incorrect important functionality in that technique (e.g., as defined in source code, object code, or other non-transitory computer readable instructions). Ideally a regression test suite would be run every night, to ensure the accuracy of the developed techniques. As described above in connection to technique 900, the validation can be thought of as distinguishing between "passing" geometry generated by encoder structure 911 and "non-passing" geometry generated by the same. In general, "passing" and "non-passing" labels involve a level of subjectivity which may prove disadvantageous according to particular implementations. Instead, regression testing can be used to test the quality of the code that automates the production of the geometry which is used to create dental or orthodontic appliances.

In other words, regression tests are used to determine whether recent changes to the system (whether in the source code, neural networks, or inputs) have negatively affected the outputs of a system. For instance, where the predictive quality of the neural network declines would be considered to be a negative effect. In the present disclosure, there is a need to be able to change a few lines of the automation code and rapidly determine whether those changes have had any adverse effects on the outputs on our suite of test cases. There may be dozens of test cases. The outputs of the dozens of test cases can be inspected manually, but at great cost in terms of the time required for a technician or other person to manually inspect the outputs for all test cases. The advantage of the present implementation is to streamline the process. Even if 1 out of 36 test cases fails to produce acceptable results after the code change, using a set of regression tests would detect that error and alert a user of the system 100 accordingly.

Figure 10:
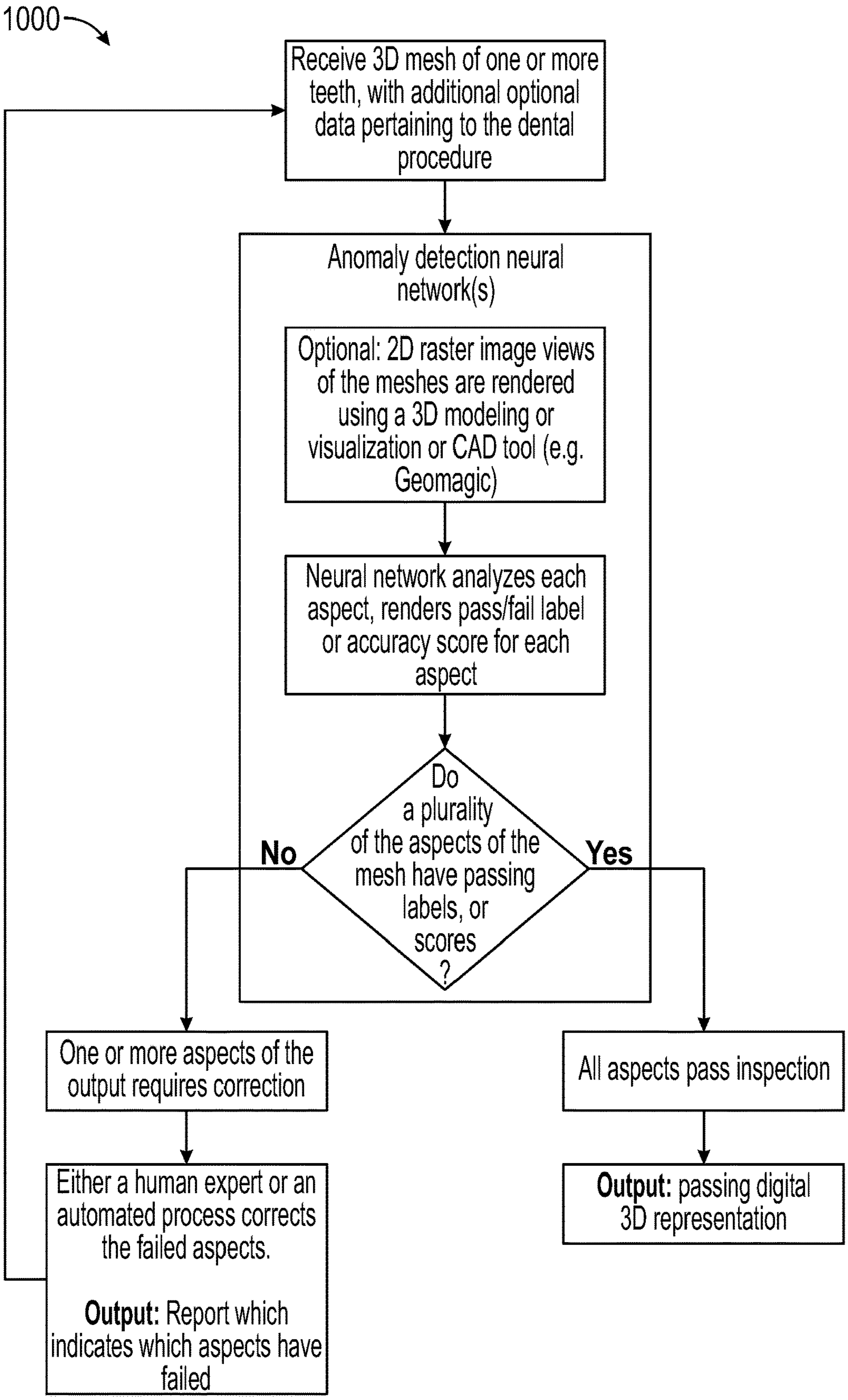
FIG. 10 shows an example generalized technique for performing validation of outputs generated by machine learning models, in accordance with various aspects of this disclosure.

FIG. 10 pertains specifically to processes and techniques related to tooth segmentation. In general, tooth segmentation involves converting a scan of a patient's dentition into a 3D representation that includes individualized components (e.g., each tooth and associated gingival tissue) for the patient's mouth. The segmented 3D representation can then be used to solve other technical problems described herein, such as generating clear tray aligners, to name one example, as well as other technical problems not specifically mentioned herein.

As a result, tooth segmentation typically first involves generating an intraoral scan of a patient's dentition. This scan yields a continuous (or a homogenous) 3D mesh that encompasses all relevant teeth and portions of the patient's gums as a single 3D representation. Additionally, and according to particular implementations, the upper and lower arches of the patient are scanned separately, and each yields a 3D mesh for the entire arch, respectively. Because "raw" scan data (which encompasses all scanned teeth and portions of the gums) is generally not deemed to be as useful in view of segmented 3D mesh data, automatic tooth segmentation techniques can be used to generate the 3D mesh data describing individual teeth of the patient's mouth, for example. In general, it is this segmented 3D data that can be used as described throughout this disclosure.

For some implementations, individual teeth are segmented, yielding a labeled mesh for each tooth. Other implementations may require that the segmentation follows the gingiva, after which an offset into the gums is defined, for the purpose of removing excess mesh material. Other implementations may require segmentation that defines a trimline that is offset into the gums, for the purpose of removing excess mesh material. Other implementations may require that a facial-lingual segmentation be performed, separating the fronts from the backs of the teeth, for the purpose of assisting in the calculation of a mold parting surface (i.e., a generated component used in the production of a dental restoration appliance), to name one example.

Figure 9:
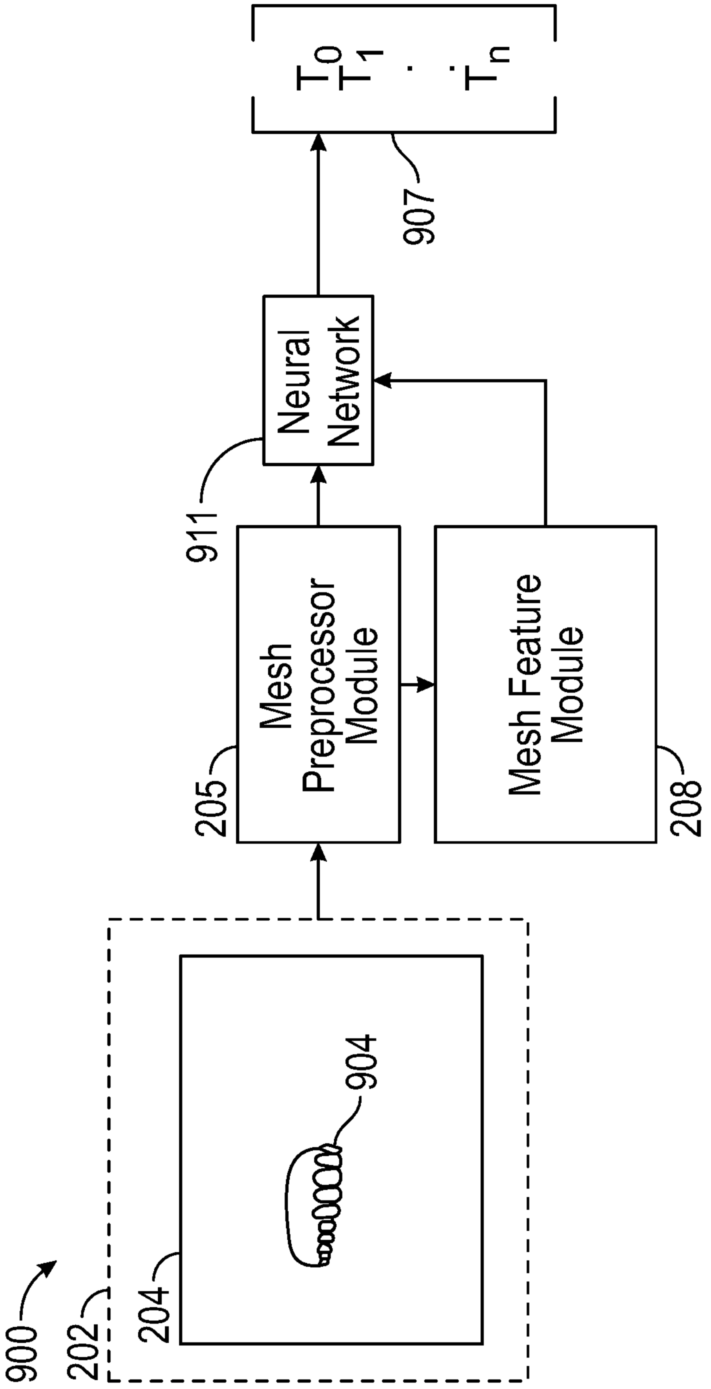
FIG. 9 shows an example technique for tooth segmentation.

FIG. 9 illustrates an example technique 900 that utilizes a trained ML model to perform a mesh segmentation. This implementation using a U-Net architecture, but other implementations are possible, such as using a MeshCNN. According to particular implementations, the ML model can be a neural network, or another ML model as appropriate. As shown in the depicted example, technique 900 can also utilize the receiving module 202 to receive patient data 204, which can include mesh data 904. In one implementation, the mesh data 904 can include one or more of the following: 1) one or more segmented whole (or complete) arches of teeth for a patient, including the gingiva; 2) one or more segmented portions of an arch for a patient, including gingiva; and 3) one or more individual segmented teeth for the patient, with or without the gingiva. This data is collectively referred to herein as one or more segmented arches of the patient's dentition.

Technique 900 also utilizes modules from technique 200, including mesh preprocessor 205 and mesh feature module 208. Instead of using an encoder structure as a generator, as show in other techniques, technique 900 uses a U-Net architecture 911 as a generator, which can include a neural network to generate predicted outputs 207, such as one or more predicted labels 907. Technique 900 may in some implementations be used for mesh segmentation, when 911 is a U-Net architecture, and 907 is a list of mesh element labels. That said, U-Net architecture 911 can also be replaced with an encoder structure, or other machine leaning models, including neural networks, such as a MeshCNN, and other neural networks. In some implementations the predicted labels 1007 can be defined as one-hot vectors. Technique 900 may in some implementations be used for 3D validation of a mesh segmentation operation, when 911 is an encoder structure, and 907 is a one-hot vector of probabilities. Technique 900 may in some implementations be used for 2D validation of a mesh segmentation operation, when 911 is a CNN, and 907 is a one-hot vector of probabilities. These implementations for 3D validation and 2D validation for mesh segmentation also apply to the other validation examples, such as mesh cleanup validation, coordinate system validation, dental restoration validation, 3D printed parts validation, fixture model validation, CTA trimline validation, dental restoration appliance component validation, and the validation of the placement of brackets and attachments for orthodontic treatment. For instance, according to one implementation, the one-hot vector of output predictions contains two elements, one containing the probability that the input mesh(es) received the predicted label of "correct," and the other containing the probability that the input mesh(es) received the predicted label of "incorrect." In one example, the one-hot vector which is output from the encoder may be of the form: [probability correct, probability incorrect]. Thus, if the actual vector generated by the encoder is [0.89, 0.11], then the meaning of this vector is that the input mesh was correct. In the "correct" case, the mesh segmentation operation is deemed a success, and the teeth are accurately separated from the gingiva and each other, in support of operations to produce dental or orthodontic appliances. In the "incorrect" case, the teeth are not accurately separated from the gingiva and further work, or revision may need to be completed, either by a technician or by a further iteration of the automated process which produced the geometry originally (e.g., the tooth segmentation algorithm described herein).

To accommodate subsequent iterations of the validation, in some implementations, the U-Net is further trained on the basis of the validation results. Furthermore, in some implementations, the ML model may examine the mesh segmentation job that has been done for each individual tooth, yielding localized feedback on the segmentation quality on a tooth-by-tooth basis. The example segmentation shown in example FIG. 9 is considered well-formed. That is, the teeth are accurately divided from the gingiva and each other. As a result, if the system 100 were to receive a similar mesh data 904, application of the encoder U-Net architecture 907 would yield a predicted label of "pass" or "correct." If, however, there are sufficient number of errors in the segmentation results, the system 100 can cause technique 900 to be performed one or more additional times until the accuracy of the U-Net has been sufficiently improved such that the U-Net is capable of generating output that is "correct."

FIG. 10 shows an example generalized technique 1800 or performing validation of outputs generated by ML models, in accordance with various aspects of this disclosure. Validation ML models may be trained to process the following non-limiting list of 3D representations: 1) mesh element labels for segmentation or mesh cleanup; 2) coordinate system axes (e.g., as encoded by transforms) for a tooth; 3) a tooth restoration design; an orthodontic setup; 4) custom lingual brackets; 5) a bonding pad for a bracket (which may be generated for a specific tooth by outlining a perimeter on the tooth, specifying a thickness to form a shell, and then subtracting-out the tooth via a Boolean operation); 6) a clear tray aligner (CTA); 7) the location or shape of a trim line (e.g., such as a CTA trimline); 8) the shape or structure or poses of attachments; 9) bite ramps or slits; 10) 3D printed aligners (local thickness, reinforcing rib geometry, flap positioning, etc.); 11) 11) a 3D model of a patient's teeth and gums showing the trim line (e.g., a fixture model), data or structures related to implant placement; 12) hardware placement; 13) other types of dental restoration design (e.g., veneers, crowns, or bridges); 14) and other 3D printed parts pertaining to oral care procedures or other fields.

Technique 1000 can use the steps of receiving 3D meshes of one or more teeth, with additional optional data pertaining to the dental procedure. This information can be provided for validation to one or more anomaly detection networks. In some implementations, this can include generating one or more 2D raster view of the 3D meshes. Next, the system 100 can use a neural network to analyze each aspect of the either the 2D and/or 3D representations to render a pass/fail determination on the aspects. If a sufficient number of aspects receiving a passing accuracy score, then the representations are deemed to have passed, at which point system 100 can provide the geometry for use in other dental processes. If a sufficient number of aspects do not receive a passing accuracy score, the system 100 can generate information as to why one or more aspects of the representation failed, and in some implementations automatically train the one or more neural networks based on the results and then perform method 1000 again leverage the additional training of the neural networks to see if a passing score can be achieved. This approach to 2D validation may, in various implementations, be applied to each of the various validation applications described in this disclosure.

Technique 1000 can be performed in near real-time allowing dental professionals and other ability professionals the perform scanning and other dental procedures while the patient is in the chair, resulting in both improved results of the dental treatment and a more pleasant experience for the patient. For instance, this validation approach can be applied to the patient's intraoral scan data immediately after the intraoral scan is performed. The advantage is that the dentist can be notified if there are problems with the scan data, and in the event that the scan must be redone, the patient is available to do so (and in fact hasn't even left the chair). Detected mesh errors include holes in the mesh, incompletely scanned teeth, missing teeth, foreign materials which obscure teeth, and/or Upper/lower arches misidentified/switched. The results of validation may be displayed to the dentist (or technician) using one or more heatmaps, possibly superimposed on a model of the teeth. Problematic regions of the mesh can be highlighted in patchwork fashion, with different color coding. Disclosure pertaining to mesh cleanup describes mesh flaws which are detected in the course of mesh cleanup validation. The application of this near real time approach may also benefit from performing checks to detect these conditions, so the intraoral scan can be redone under different conditions (e.g., more careful technique by the technician or doctor). In such instances, the need for latter mesh cleanup operations may be reduced or eliminated.

Specific errors or flaws in the scan are highlighted using colors, bounding boxes, arrows or other graphical elements, and displayed to the dentist/technician. For example, if the validation engine determines that a portion of a tooth is missing from the mesh, then a bounding box can be draw onto a visualization of that mesh over the area of the missing or incomplete tooth. A text report about the quality of the scan may be prepared and sent over SMS, email or other electronic means, or displayed to the dentist/technician in the dentist's office. In some instances, there may be an LCD display located proximate to the scanner which displays the validation report to the dentist. As another example, the validation engine can apply a parting surface to a tooth results in each edge/vertex/face element in the tooth mesh being labeled as either A) facial or B) lingual: 1) facial portion of a tooth, where the parting surface that was used to cleave the tooth was located too far in the facial direction (e.g. by either 1.0 mm or 0.5 mm); 2) facial portion of a tooth, where the parting surface was correct; 3) facial portion of a tooth, where the parting surface that was used to cleave the tooth was located too far in the lingual direction (e.g. by either 1.0 mm or 0.5 mm). According to particular implementations, there may be more than one kind of label. For instance, certain implementations may use both element labels and result labels. An element label describes whether an edge/vertex/face element is on the facial side of a tooth mesh or on the lingual side of a tooth mesh. A result label indicates whether the parting surface in the vicinity of a tooth is 1) too far facial, 2) correct or 3) too far lingual, to name one example.

According to the techniques of this disclosure, an ML model may be trained on examples of 3D oral care representations where ground truth data are provided to the ML model, and loss functions are used to quantify the difference between predicted and ground truth examples. Loss values may then be used to update the validation ML model (e.g., to update the weights of a neural network). Such validation techniques may determine whether a trial 3D oral care representation is acceptable or suitable for use in creating an oral care appliance. "Acceptable" may, in some instances, mean that a trial 3D oral care representation conforms with the distribution of the ground truth examples that were used in training the ML validation model. "Acceptable" may, in some instances, mean that the trial 3D oral care representation is correctly shaped or correctly positioned relative to one or more aspects of dental anatomy.

In the example of a generated appliance component (e.g., a dental restoration appliance component, such as a mold parting surface), the techniques may determine whether the component intersects with the correct landmarks or other portions of dental anatomy (e.g., the incisal edges and cusp tips—for the mold parting surface). The techniques may also determine one or more of the following: 1) whether a CTA trimline intersect the gums in a manner that reflects the distribution of the ground truth; 2) whether a library component get placed correctly with relation to one or more target teeth (e.g., snap clamps placed in relation to the posterior teeth or a center clip in relation to the incisors), or with relation to one or more landmarks on a target tooth; 3) whether a hardware element get placed on the face of tooth, with margins which reflect the distribution of ground truth examples; 4) whether the mesh element labeling for a segmentation (or mesh cleanup) operation conform to the distribution of the labels in the ground truth examples; and 5) whether the shape and/or structure of a dental restoration tooth design conform with the distribution of tooth designs amongst the ground truth training examples, to name a few examples. Other validation conditions and/or rules are possible for the validation of various 3D oral care representations.

Figure 11:
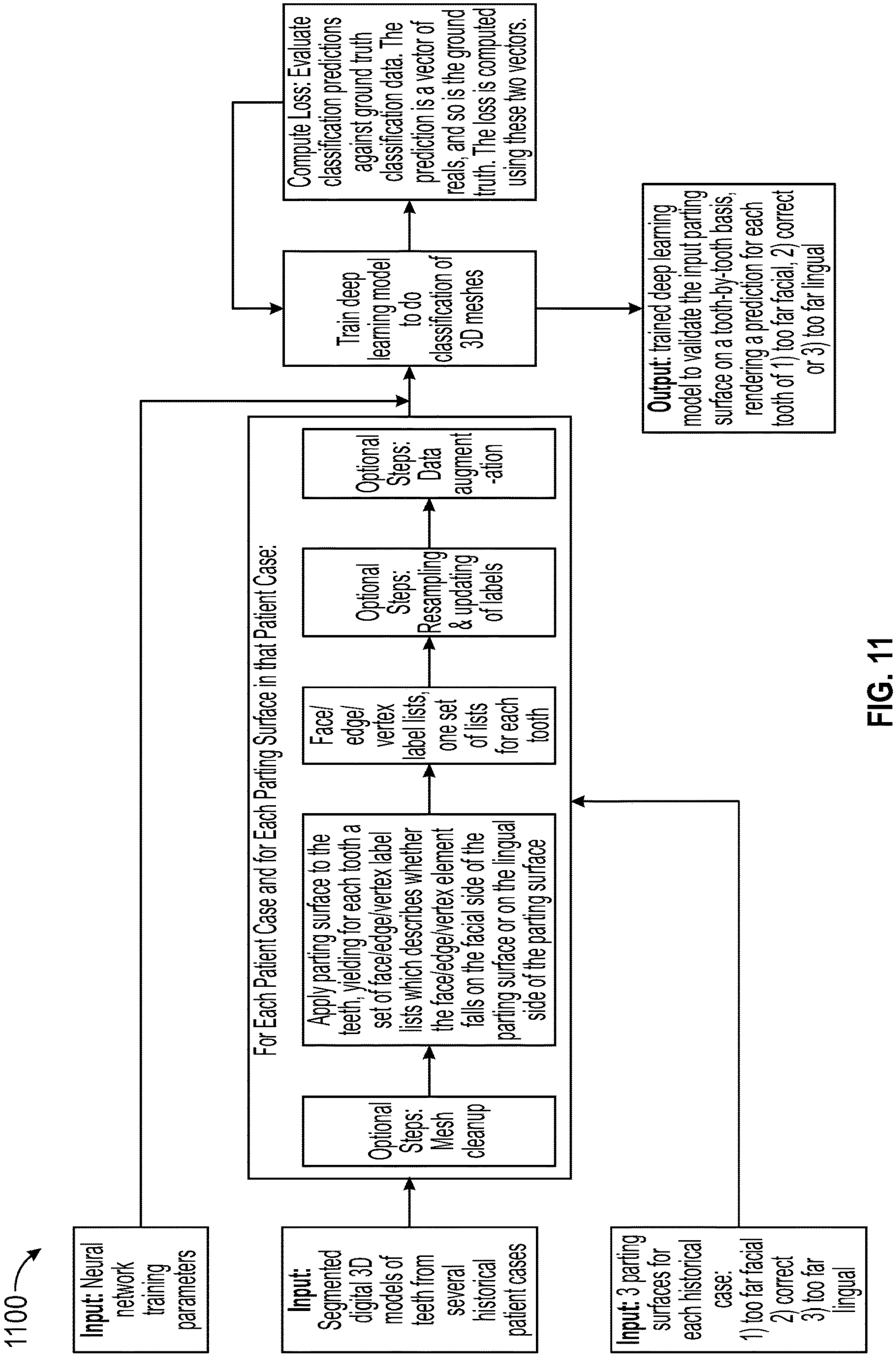
FIG. 11 shows an example technique for training a machine learning model.

FIG. 11 shows an example technique 1100 for training an ML model (e.g., to classify 3D meshes for the purpose of 3D mesh or point cloud validation). The validation systems and techniques of this disclosure may assign one or more labels to one or more aspects of a representation that is to be validated (e.g., correctly formed or placed, or incorrectly formed or placed, and the like). The validation systems and techniques of this disclosure may benefit from the computation of mesh element features. 3D oral care mesh validation can be applied to segmentation, mesh cleanup, coordinate system prediction, dental restoration design, CTA setups validation, CTA trimline validation, fixture model validation, archform validation, orthodontic hardware placement validation, appliance component placement validation, 3D printed parts validation, chairside scan validation, and other validation techniques described herein. In the event that a 3D validation check yields a failing output, then one or more instructions or feedback data may be communicated to the algorithm, process or model that created the 3D oral care representation, so that a further iteration of 3D oral care representation generation may improve the design and hopefully mitigate the conditions which led to the failure of the validation check. A neural network which is trained to classify 3D meshes (or point clouds) for validation may, in some implementations, take as input mesh element features (e.g., a mesh element feature vector may be computed for one or more mesh elements in the mesh or point cloud which is to be validated). In some instances, a mesh element feature vector may accompany each mesh element as input to a validation neural network. A validation neural network may, in some instances, form a reformatted (or sometimes reduced dimensionality) representation of an inputted mesh or point cloud. Mesh element features may improve such a reformatted (or reduced dimensionality) representation, by providing additional information about the shape and/or structure of the inputted mesh or point cloud. The data precision and accuracy of the resulting validation is improved through the use of mesh element features.

Figure 12:
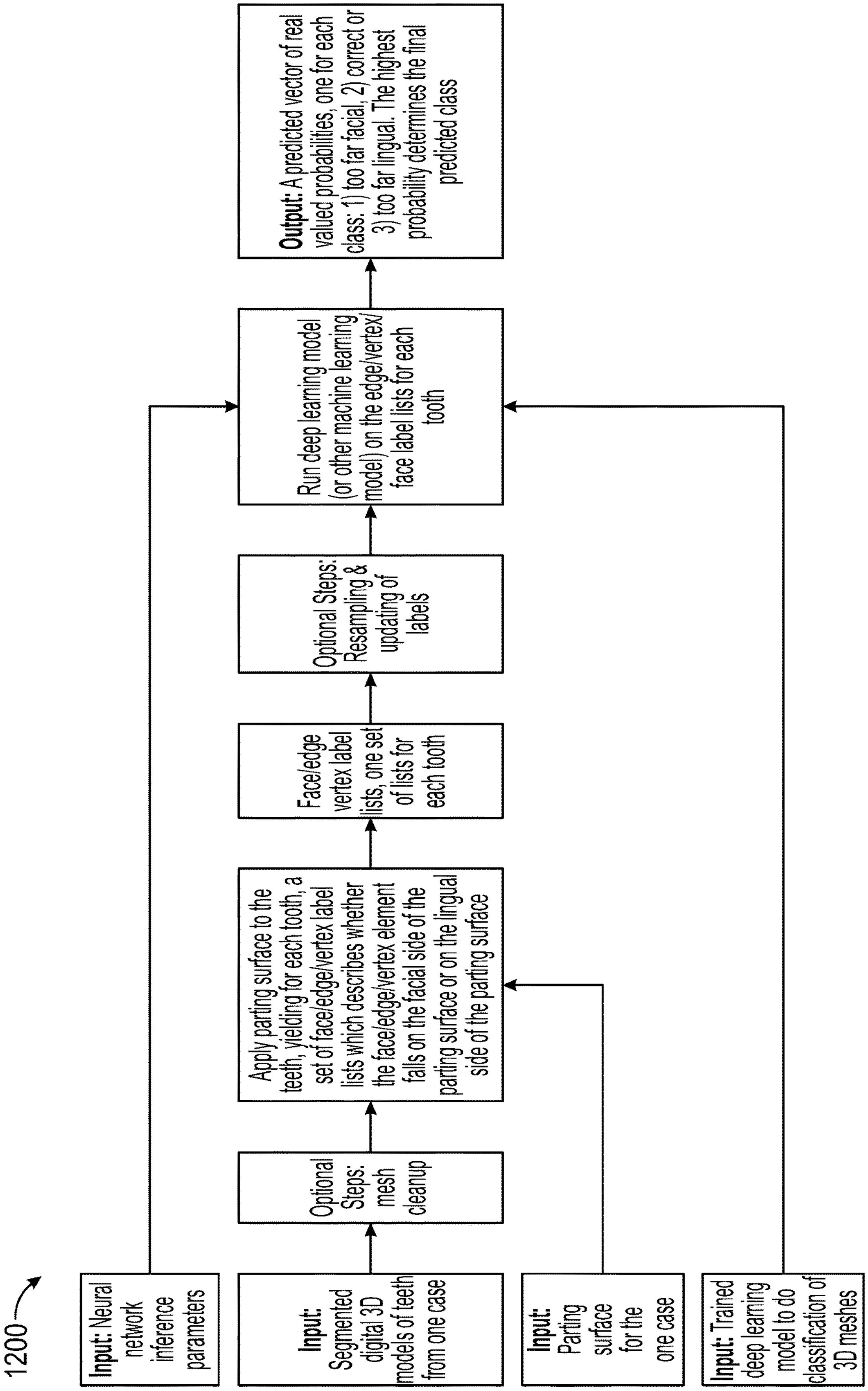
FIG. 12 shows an example technique for using a trained machine learning model to validate dental restoration appliance components, according to various aspects of this disclosure.

FIG. 12 shows an example technique 1200 for using a trained ML model to validate a dental restoration appliance component (e.g., a mold parting surface), according to various aspects of this disclosure. In some implementations, one or more teeth may be modified as a result of interacting with an appliance or appliance component, such as in the example that a mold parting surface is used to cut an arch of teeth into one or more facial portions and/or one or more lingual portions. The mold parting surface may be designed according to certain labeled classes, such as "correct" (e.g., where the parting surface approximately follows the incisal edges and at least one of the inner and outer cusp tips) or "incorrect" (e.g., where the surface has been distorted to cut the teeth in a manner that is either too far facial or too far lingual of the incisal edges and cusp tips). A neural network may be trained to classify 3D meshes representing teeth which have been cut using each of these multiple classes of parting surface, for the purpose of validating that parting surface (e.g., or some other appliance or appliance component).

Figure 13:
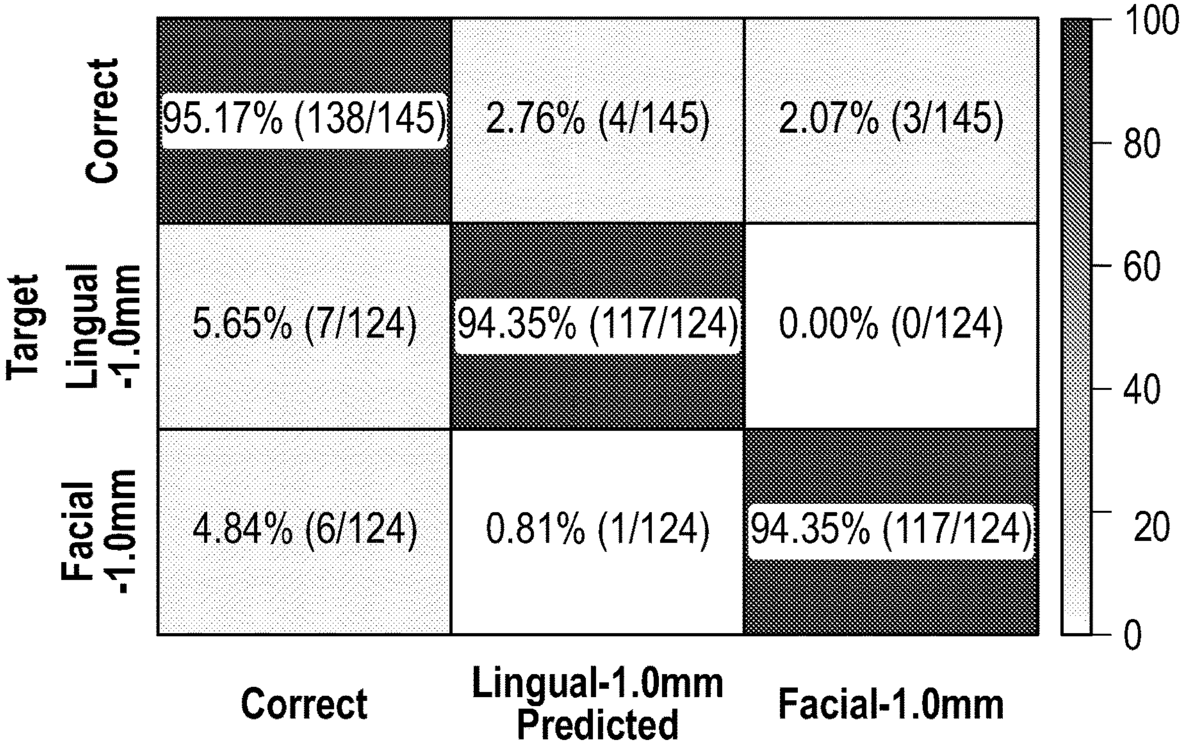
FIG. 13 illustrates possible conditions under which a mold parting surface intersects a tooth mesh.

FIG. 13 illustrates 3 possible states which a mold parting surface may exhibit with regards to a tooth. A mold parting surface is meant to divide the facial from the lingual portions of a tooth and is used in the production of a dental restoration appliance. An example of a correct partitioning of the tooth by the mold parting surface is shown in the center graphic. To the left is shown the case where a mold parting surface partitions that tooth too far in the facial direction. Finally, on the right side of the figure, is the case where a mold parting surface partitions the tooth too far in the lingual direction. The table in the figure shows the performance results of a 3D mesh validation neural network which was trained on 3D meshes of teeth which had been subdivided by parting surfaces. Each of the three classes were represented in the dataset. The accuracy figures report the ability of this 3D validation neural network to identify each of the three classes. This 3D validation neural network used an Encoder to perform the mesh classification. Other implementations of 3D validation may use a MeshCNN. This example of 3D validation for a dental restoration appliance component (i.e., the mold parting surface) also applies to each of the other validation applications described in this disclosure. The other 3D validation applications can train a neural network (e.g., and encoder) in a similar fashion, with meshes which represent different categories. Applications include segmentation validation, mesh cleanup validation, coordinate system validation, CTA trimline validation, orthodontic setups validation, dental restoration design validation, bracket/attachment placement validation, validation of 3D printed parts and fixture model validation.

Various aspects of the disclosure can be used for different purposes across the one or more digital dentistry domain including segmentation, coordinate systems, mesh cleanup, setups for clear tray aligners, dental restoration appliances, brackets and attachments, 3D printed parts, restoration design, and fixture models. These domains may involve both the generation of one or more (2D or 3D) representations as well as the validation of one or more (2D or 3D) representation. One or more of these domains can be combined, for example, certain techniques may combine concepts form 1) segmentation, 2) the computation of geometry for dental restoration appliance, and 3) mesh validation. For instance, the results of facial-lingual segmentation can be consumed by an algorithm which generates the mold parting surface, with the intention of improving the resulting mold parting surface (i.e., relative to mold parting surfaces which would be generated without the benefit of prior facial-lingual segmentation). The resulting mold parting surface may then be inspected by a validation module (i.e., using either 2D or 3D processing). If the validation module determines that the generated mold parting surface is inferior, then the algorithm which generates the mold parting surface can be re-run, potentially using actionable feedback from the validation engine (e.g., hints about how to adjust the mold parting surface on a tooth-by-tooth basis, whether the parting surface should move in the facial direction or in the lingual direction in the vicinity of each tooth). If the validation module determines that the generated mold parting surface is acceptable, then the mold parting surface is outputted.

While this specification sets forth many specific implementation details, these should not be construed as limitations on the scope of what may be claimed, but rather as descriptions of features that may be specific to particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the implementations described above should not be understood as requiring such separation in all implementations, and it should be understood that the described components and systems can generally be integrated together in a single system or distributed across multiple systems.

What is claimed is:

1. A computer-implemented method for using one or more machine learning models to automatically validate one or more characteristics of a digital representation of a dental restoration appliance component, the method comprising:

receiving, by one or more computer processors, a first digital 3D oral care representation of an appliance component;

receiving, by the one or more computer processors, a first digital 3D oral care representation of one or more teeth of a patient;

using, by the one or more computer processors, a machine learning model, of the one or more machine learning models, to assign one or more result labels to the first digital 3D oral care representation of the appliance component, wherein the one or more result labels specify whether the appliance component is incorrectly formed or incorrectly placed;

analyzing, by the one or more computer processors, the one or more result labels;

automatically generating, by the one or more computer processors, output that specifies whether the appliance component is incorrectly formed or incorrectly placed;

receiving, by the one or more computer processors, validation feedback information associated with the output, wherein the validation feedback information indicates whether the output correctly reflects an actual suitability of the appliance component for use; and automatically retraining, by the one or more computer processors, the machine learning model based on the validation feedback information, wherein the retrained machine learning model is used to assign result labels to subsequent digital representations of dental restoration appliance components.

2. The computer-implemented method of claim 1, wherein at least one of the one or more machine learning models is a neural network.

3. The computer-implemented method of claim 1, wherein automatically retraining the machine learning model comprises adjusting one or more weights of the machine learning model based on the validation feedback information.

4. The computer-implemented method of claim 1, wherein the machine learning model has been trained to classify 3D oral care representations.

5. The computer-implemented method of claim 1, further comprising computing, by the one or more computer processors, at least one landmark for at least one tooth, and wherein the first digital 3D oral care representation is generated or placed, at least in part, based on the at least one landmark.

6. The computer-implemented method of claim 1, wherein the first digital 3D oral care representation is generated or placed by a second machine learning model which comprises one or more neural networks.

7. The computer-implemented method of claim 1, wherein the first digital 3D oral care representation of the appliance component is generated according to a specific nature of a dental anatomy of the patient.

8. The computer-implemented method of claim 1, wherein the first digital 3D oral care representation of the appliance component comprises a prefabricated digital component placed in relation to a dental anatomy of the patient.

9. The computer-implemented method of claim 8, wherein the one or more result labels that specify whether the appliance component is incorrectly placed specify whether the appliance component is incorrectly placed relative to the dental anatomy of the patient.

10. The computer-implemented method of claim 1, further comprising generating, by the one or more computer processors and when it is determined, based on the analyzing, that the appliance component is incorrectly formed or incorrectly placed, one or more suggestions of how to correct the first digital 3D oral care representation.

11. The computer-implemented method of claim 1, wherein one or more two dimensional (2D) representations are generated based at least in part on the first digital 3D oral care representation.

12. The method of claim 11, wherein the machine learning model is trained to classify the one or more 2D representations.

13. The computer-implemented method of claim 1, further comprising automatically generating, by the one or more computer processors, output that specifies whether the first digital 3D oral care representation is correctly formed or correctly placed.

14. The computer-implemented method of claim 13, wherein when it is determined based on the analyzing, that the first digital 3D oral care representation has not been correctly formed or correctly placed, sending, by the one or more computer processors, a command to re-run at least: a process to generate an appliance component or a process to place an appliance component.

15. The computer-implemented method of claim 1, wherein the method is performed in real-time while the patient is present in a clinical environment.

16. A system comprising:

one or more computer processors;

non-transitory computer-readable storage having stored thereon one or more neural networks to automatically validate geometrical characteristics of a digital representation of a dental restoration appliance component and instructions that when executed by the one or more computer processors cause the one or more computer processors to:

receive a first digital 3D oral care representation of an appliance component;

receive a first digital 3D oral care representation of one or more teeth of a patient;

use a machine learning model to assign one or more result labels to the first digital 3D oral care representation of an appliance component, wherein the one or more result labels specify whether the appliance component is incorrectly formed or incorrectly placed;

analyze the one or more result labels;

automatically generate output that specifies whether the appliance component is incorrectly formed or incorrectly placed;

receive validation feedback information associated with the output, wherein the validation feedback information indicates whether the output correctly reflects an actual suitability of the appliance component for use; and automatically retrain the machine learning model based on the validation feedback information, wherein the retrained machine learning model is used to assign result labels to subsequent digital representations of dental restoration appliance components.

17. The system of claim 16, wherein the instructions are executed in real-time while the patient is present in a clinical environment.

18. The system of claim 16, wherein at least one of the one or more machine learning models is a neural network.

19. The system of claim 16, wherein, to automatically retrain the machine learning model, the instructions that when executed by the one or more computer processors cause the one or more computer processors to adjust one or more weights of the machine learning model based on the validation feedback information.

20. The system of claim 16, wherein the output further specifies whether the first digital 3D oral care representation is correctly formed or correctly placed.

* * * * *